United States Patent
Byk et al.

(10) Patent No.: US 6,171,612 B1
(45) Date of Patent: Jan. 9, 2001

(54) LIPOPOLYAMINES AS TRANSFECTION AGENTS AND PHARMACEUTICAL USES THEREOF

(75) Inventors: Gérardo Byk, Creteil; Daniel Scherman, Paris; Bertrand Schwartz, Maisons Alfort; Catherine Dubertret, Sevres, all of (FR)

(73) Assignee: Aventis Pharma S.A., Antony (FR)

( * ) Notice: Under 35 U.S.C. 154(b), the term of this patent shall be extended for 0 days.

(21) Appl. No.: 09/068,753
(22) PCT Filed: Nov. 8, 1996
(86) PCT No.: PCT/FR96/01774
§ 371 Date: May 13, 1998
§ 102(e) Date: May 13, 1998
(87) PCT Pub. No.: WO97/18185
PCT Pub. Date: May 22, 1997

(30) Foreign Application Priority Data

Nov. 14, 1995 (FR) .................................... 9513490

(51) Int. Cl.$^7$ .................................... A61K 9/127
(52) U.S. Cl. ................. 424/450; 424/121; 424/9.321; 424/9.51; 935/54; 514/44; 564/225; 564/226
(58) Field of Search ................. 424/450, 1.21, 424/9.321, 9.51, 94.3; 436/829; 935/54; 514/44; 554/104; 564/225, 226

(56) References Cited

U.S. PATENT DOCUMENTS

| 5,476,962 | 12/1995 | Behr et al. |
| 5,616,745 | * 4/1997 | Behr .................................... 554/56 |
| 5,837,533 | * 11/1998 | Boutin .............................. 435/320.1 |

FOREIGN PATENT DOCUMENTS

| 0394111 | 10/1990 | (EP) . |
| 9405624 | 3/1994 | (WO) . |
| 9518863 | 7/1995 | (WO) . |
| 9625508 | 8/1996 | (WO) . |

* cited by examiner

Primary Examiner—Gollamudi S. Kishore
(74) Attorney, Agent, or Firm—Comolly, Bove, Lodge & Hutz LLP

(57) ABSTRACT

Lipopolyamines useful for the transfection of nucleic acid and methods of preparation thereof are disclosed. The lipopolyamines are of general formula I, in which R4 comprises at least one C10–C22 aliphatic radical.

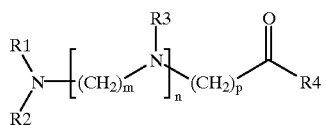

34 Claims, 3 Drawing Sheets

SEQUENCE LISTING

```
<160> NUMBER OF SEQ ID NOS:  2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: COMPLETELY
      SYNTHESIZED

<400> SEQUENCE: 1

Lys Thr Pro Lys Lys Ala Lys Lys Pro
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: COMPLETELY
      SYNTHESIZED

<400> SEQUENCE: 2

Ala Thr Pro Ala Lys Lys Ala Ala
 1               5
```

LIPOPOLYAMINES AS TRANSFECTION AGENTS AND PHARMACEUTICAL USES THEREOF

This application is a 371 of PCT/FR96/01774 filed Nov. 8, 1996.

The present invention relates to novel compounds similar to the family of lipopolyamines, to pharmaceutical compositions containing them, to their applications for the in vivo and/or in vitro transfection of nucleic acids and to a process for their preparation.

Many genetic diseases are associated with an expression defect and/or abnormal expression, that is to say deficient or excessive expression, of one or more nucleic acids. The main aim of gene therapy is to correct genetic abnormalities of this type by means of the in vivo or in vitro cellular expression of cloned genes.

Today, several methods are proposed for the intracellular delivery of this type of genetic information. One of them in particular is based on the use of chemical or biochemical vectors. Synthetic vectors have two main functions, to compact the DNA to be transfected and to promote its cellular binding as well as its passage across the plasma membrane and, if necessary, across the two nuclear membranes.

Considerable progress has been achieved in this mode of transfection, with the development of technology based on the use of a cationic lipid. It has thus been demonstrated that a positively charged cationic lipid, N-[1-(2,3-dioleyloxy)propyl]-N,N,N-trimethylammonium chloride (DOTMA), interferes spontaneously, in the form of liposomes or small vesicles, with DNA, which is negatively charged, to form lipid-DNA complexes, which are capable of fusing with cell membranes, and thus allows the intracellular delivery of DNA. However, although this molecule is effective in terms of transfection, it has the drawback of being non-biodegradable and of having a toxic nature with regard to cells.

Since DOTMA, other cationic lipids have been developed along the lines of this structural model: lipophilic group combined with an amino group via a so-called "spacer" arm. Among these, mention may be made more particularly of those comprising, as lipophilic group, two fatty acids or a cholesterol derivative, and additionally containing, if necessary, as amino group, a quaternary ammonium group. DOTAP, DOBT and ChOTB may be mentioned in particular as representatives of this category of cationic lipids. Other compounds, for instance DOSC and ChOSC, are characterized by the presence of a choline group in place of the quaternary ammonium group. In general, however, the transfecting activity of these compounds remains fairly low.

Another category of cationic lipids, lipopolyamines, has also been described. For the purposes of the present invention, the term lipopolyamine denotes an amphiphilic molecule comprising at least one hydrophilic polyamine region combined, via a so-called spacer region, with a lipophilic region. The polyamine region of lipopolyamines, which are cationically charged, is capable of combining reversibly with nucleic acid, which is negatively charged. This interaction compacts the nucleic acid greatly. The lipophilic region renders this ionic interaction insensitive to the external medium, by coating the nucleolipid particle formed with a lipid film. In compounds of this type, the cationic group may be represented by the L-5-carboxyspermine radical which contains four ammonium groups, two primary and two secondary. DOGS and DPPES are in particular among the compounds of this type. These lipopolyamines are most particularly effective for transfecting primary endocrine cells.

In point of fact, an ideal synthetic transfecting agent should display a high level of transfection, and should do so for a broad spectrum of cells, should have no toxicity or, failing that, a very minimal toxicity at the doses used, and, lastly, should be biodegradable so as to be rid of any side-effects on the cells treated.

The object of the present invention is, precisely, to propose novel lipopolyamines, which are original on the basis of their polyamine fraction, and which can be used effectively in the in vitro and/or in vivo transfection of cells and in particular for the vectorization of nucleic acids.

A first subject of the present invention is lipopolyamines, in D, L or D,L form and their salts, characterized in that they are represented by the general formula I

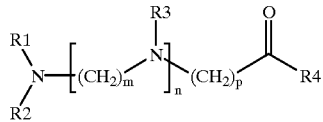

in which:
R1, R2 and R3 represent, independently of each other, a hydrogen atom or a group —(CH$_2$) q—NRR' with
q able to range between 1, 2, 3, 4, 5 and 6, and doing so independently between the various groups R1, R2 and R3 and
R and R' representing, independently of each other, a hydrogen atom or a group —(CH$_2$)q'—NH$_2$, q being able to range between 1, 2, 3, 4, 5 and 6, and doing so is independently between the various groups R and R',
m, n and p represent, independently of each other, an integer which may vary between 0 and 6 with, when n is greater than 1, m able to take different values and R3 able to take different meanings within the general formula I, and
R4 represents a group of general formula II

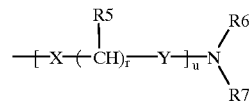

in which:
R6 and R7 represent, independently of each other, a hydrogen atom or a saturated or unsaturated C10 to C22 aliphatic radical with at least one of the two groups being other than hydrogen,
u is an integer chosen between 0 and 10 with, when u is an integer greater than 1, R5, X, Y and r able to have different meanings within the different units [X—(CHR5)r—Y]
X represents an oxygen or sulphur atom or an amine group which may or may not be monoalkylated,
Y represents a carbonyl group or a methylene group R5 represents a hydrogen atom or a side chain of a natural amino acid, which is substituted if necessary, and
r represents an integer ranging between 1 and 10 with, when r is equal to 1, R5 representing a side chain of a natural amino acid and, when r is greater than 1, R5 representing a hydrogen atom.

For the purposes of the invention, the expression side chain of a natural amino acid is understood in particular to denote chains containing amidinium units such as, for example, the side chain of arginine. As mentioned above, this chain may be substituted with saturated or unsaturated, linear, branched or cyclic C1 to C24 aliphatic groups such as, for example, cholesteryl, arachidonyl or retinoyl radicals and mono- or polyaromatic groups such as, for example, benzyloxycarbonyl derivatives, benzyl ester derivatives and substituted or unsubstituted rhodaminyl derivatives.

These novel products of general formula (I) may be in the form of non-toxic and pharmaceutically acceptable salts. These non-toxic salts comprise salts with inorganic acids (hydrochloric acid, sulphuric acid, hydrobromic acid, phosphoric acid and nitric acid) or with organic acids (acetic acid, propionic acid, succinic acid, maleic acid, hydroxymaleic acid, benzoic acid, fumaric acid, methanesulphonic acid and oxalic acid) or with inorganic bases (sodium hydroxide, potassium hydroxide, lithium hydroxide and lime) or organic bases (tertiary amines such as triethylamine, piperidine and benzylamine).

Representatives of the compounds according to the invention which may be mentioned more particularly are the compounds of the following general sub-formulae:

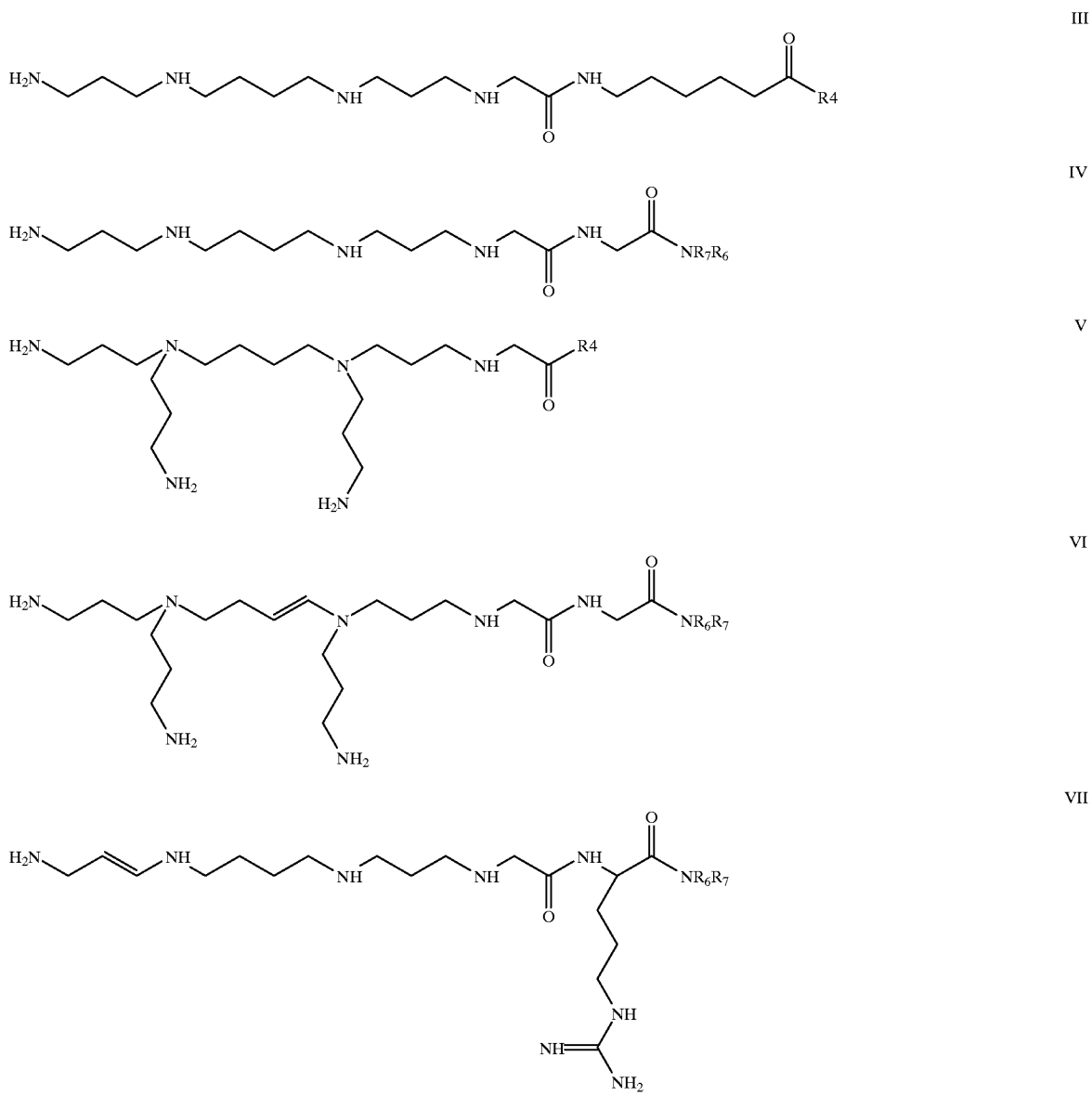

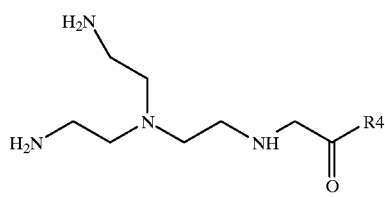

VIII

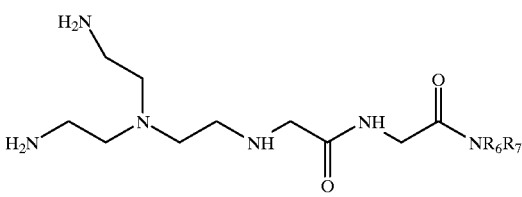

IX

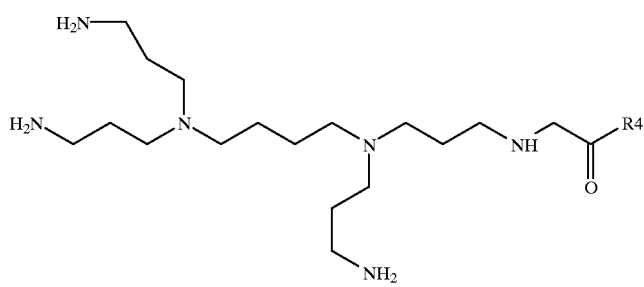

X

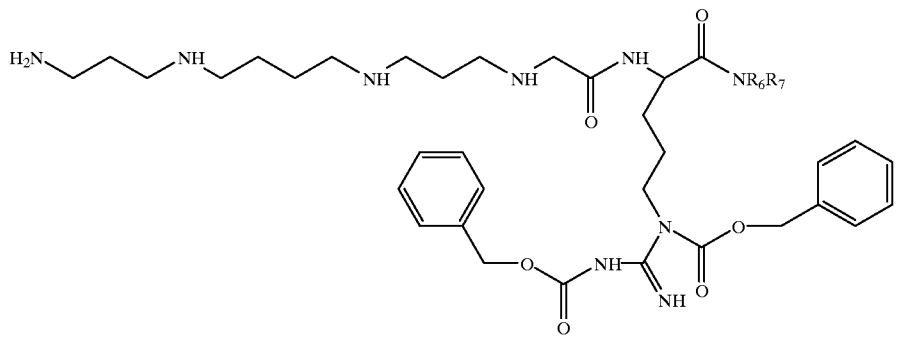

XI

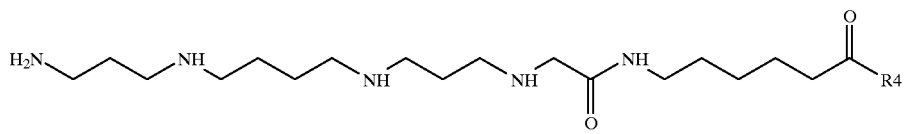

XII in which R4, R6 and R7 have the above definitions. Preferably, R4 represents therein an NR6R7 group with R6 and R7 appearing in subformulae III to XII as an identical group chosen from $(CH_2)_{17}CH_3$, $(CH_2)_{11}CH_3$, $(CH_2)_{13}CH_3$ or $(CH_2)_{12}CH_3$.

In a particularly advantageous embodiment, the compounds claimed also comprise a targeting element which makes it possible to direct the transfer of the nucleic acid with which they are combined. This targeting element is preferably incorporated, on the compound of general formula I, in the amino acid side chain featured by the substituent R5. More preferably, the targeting element is attached, covalently or non-covalently, to the compound according to the invention.

This element may be an extracellular targeting element which makes it possible to direct the transfer of the nucleic acid towards certain desired cell types or certain desired tissues (tumour cells, liver cells, haematopoietic cells, etc.). In this respect, it may be a cell receptor ligand present at the surface of the target cell type such as, for example, a sugar, a folate, a transferrin, an insulin, an asialo-orosomucoid protein or any bioactive molecule recognized by extracellular receptors. It may also be an intracellular targeting element which makes it possible to direct the transfer of the nucleic acid towards certain preferred cell compartments (mitochondria, nucleus, etc.), such as, for example, a nuclear localization signal sequence (nls) which promotes the accumulation of transfected DNA in the nucleus.

More generally, the targeting elements which an be used within the context of the invention include sugars, peptides, oligonucleotides, steroids and lipids. They are preferably sugars and/or peptides such as antibodies or antibody fragments, cell receptor ligands or fragments thereof, receptors or receptor fragments, etc. In particular, they may be ligands for growth factor receptors, for cytokine receptors, for cell lectin receptors or for receptors for adhesion proteins such as integrins. Mention may also be made of the receptor for transferrin, for HDL lipids and for LDL lipids. The targeting element may also be a sugar which makes it possible to target lectins such as asialoglycoprotein receptors, or alternatively an antibody Fab fragment which makes it possible to target the immunoglobulin Fc fragment receptor.

Similarly, it is possible to envisage the combination of a labelling agent of biotin, rhodamine or folate type with a compound of general formula I, for example on the amino acid side chain R5. This labelling agent may also be a linear or cyclic peptide or pseudopeptide sequence containing the epitope Arg-Gly-Asp for recognition of the primary and/or secondary receptors of adhesion proteins of the integrin type.

Illustrations of the lipopolyamines claimed, which may be mentioned more particularly are the following compounds, which are described in greater detail in the examples below:

$H_2N(CH_2)_3NH(CH_2)_4NH(CH_2)_3NHCH_2COGyN[(CH_2)_{17}-CH_3]_2$ $H_2N(CH_2)_3NH(CH_2)_4NH(CH_2)_3NHCH_2CON[(CH_2)_{17}-CH_3]_2$ $H_2N(CH_2)_3NH(CH_2)_4NH(CH_2)_3NHCH_2COArgN[(CH_2)_{17}-CH_3]_2$ $H_2N(CH_2)_3NH(CH_2)_4NH(CH_2)_3NHCH_2COArg(Z)_2N[(CH_2)_{17}-CH_3]_2$ $H_2N(CH_2)_3NH(CH_2)_4NH(CH_2)_3NHCH_2COLys(rhodamine)N[(CH_2)_{17}-CH_3]_2$ $H_2N(CH_2)_3NH(CH_2)_4NH(CH_2)_3NHCH_2COLys(biotinyl)N[(CH_2)_{17}-CH_3]_2$ $\{(H_2N(CH_2)_3\}_2N(CH_2)_4N\{(CH_2)_3NH_2\}(CH_2)_3NHCH_2COGlyN[(CH_2)_{17}-(CH_3]_2$ $\{H_2N(CH_2)_3\}_2N(CH_2)_4N\{(CH_2)_3NH_2\}(CH_2)_3NHCH_2CON[(CH_2)_{17}-CH_3]_2$ $\{H_2N(CH_2)_2\}_2N(CH_2)_2NHCH_2COGlyN[(CH_2)_{17}-CH_3]_2$ $\{_2N(CH_2)_2\}_2N(CH_2)_2NHCH_2CON[(CH_2)_{17}-CH_3]_2$ $NH_2(CH_2)_3NH(CH_2)_4N[(CH_2)_3NH_2]CH_2COGlyN[(CH_2)_{17}CH_3]_2$ $NH_2(CH_2)_3NH(CH_2)_4NH(CH_2)_3NHCH_2COLysN[(CH_2)_{17}CH_3]_2$ $NH_2(CH_2)_3NH(CH_2)_4NH(CH_2)_3NHCH_2COLYS[Cl-Z]N[(CH_2)_{17}CH_3]_2$ $NH_2(CH_2)_3NH(CH_2)_4NH(CH_2)_3NHCH_2COLys[CHO]N[(CH_2)_{17}CH_3]_2$ $NH_2(CH_2)_3NH(CH_2)_4NH(CH_2)_3NHCH_2COLys[Cholesteryl]N[(CH_2)_{17}CH_3]_2$ $NH_2(CH_2)_3NH(CH_2)_4NH(CH_2)_3NHCH_2COLys[Arachidonyl]N[(CH_2)_{17}CH_3]_2$ $NH_2(CH_2)_3NH(CH_2)_4NH(CH_2)_3NHCH_2COGluN[(CH_2)_{17}CH_3]_2$ $NH_2(CH_2)_3NH(CH_2)_4NH(CH_2)_3NHCH_2COGlu[N(CH_3)_2]N[(CH_2)_{17}CH_3]_2$ $NH_2(CH_2)_3NH(CH_2)_4NH(CH_2)_3NHCH_2COGlu[O-Bz]N[(CH_2)_{17}CH_3]_2$ $NH_2(CH_2)_3NH(CH_2)_4NH(CH_2)_3NHCH_2COGlu[Galactosamide]N[(CH_2)_{17}CH_3]_2$ $NH_2(CH_2)_3NH(CH_2)_4NH(CH_2)_3NHCH_2COGlu[Glucosamide]N[(CH_2)_{17}CH_3]_2$ $NH_2(CH_2)_3NH(CH_2)_4NH(CH_2)_3NHCH_2COGlu[Mannosamide]N[(CH_2)_{17}CH_3]_2$ $NH_2(CH_2)_3NH(CH_2)_4NH(CH_2)_3NH(CH_2)_3CON[(CH_2)_{17}CH_3]_2$ $NH_2(CH_2)_3NH(CH_2)_4NH(CH_2)_3NHCH_2CONH(CH_2)_5CON[(CH_2)_{17}CH_3]_2$ $NH_2(CH_2)_3NH(CH_2)_4NH(CH_2)_3NHCH_2COGlyN[(CH_2)_{11}CH_3]_2$ $NH_2(CH_2)_3NH(CH_2)_4NH(CH_2)_3NHCH_2COGlyN[(CH_2)_{12}CH_3]_2$ and $NH_2(CH_2)_3NH(CH_2)_4NH(CH_2)_3NHCH_2COGlyN[(CH_2)_{13}CH_3]_2$.

Compounds which are particularly representative of the present invention and which may be mentioned more particularly [lacuna] whose general formula is represented below.

(6)
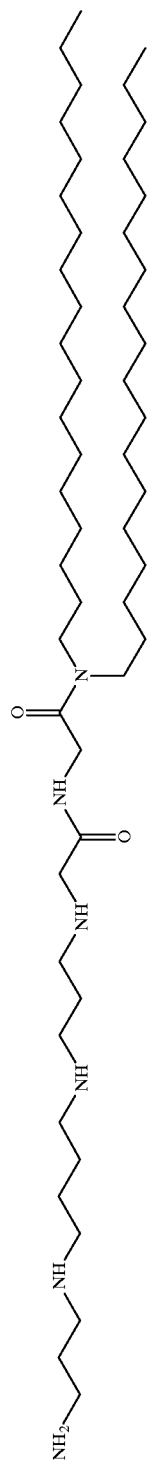
RPR120535
(21)
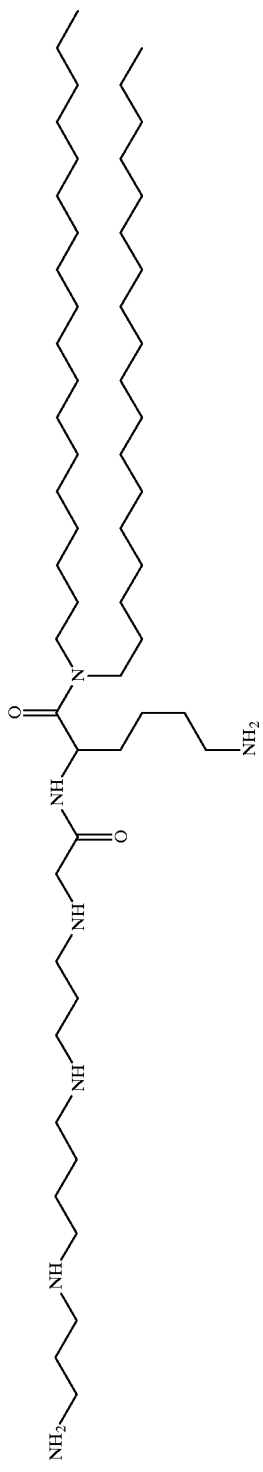
RPR127888A
(22)
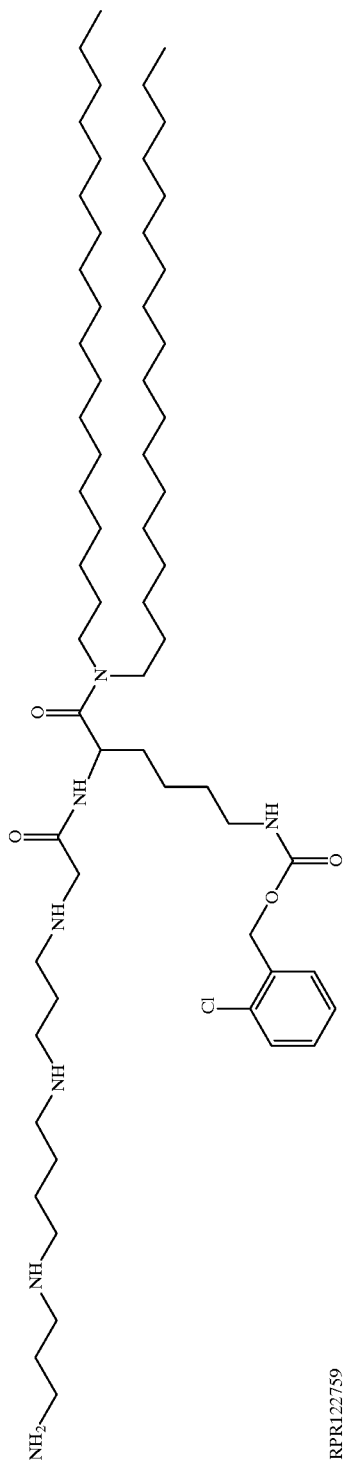
RPR122759

-continued
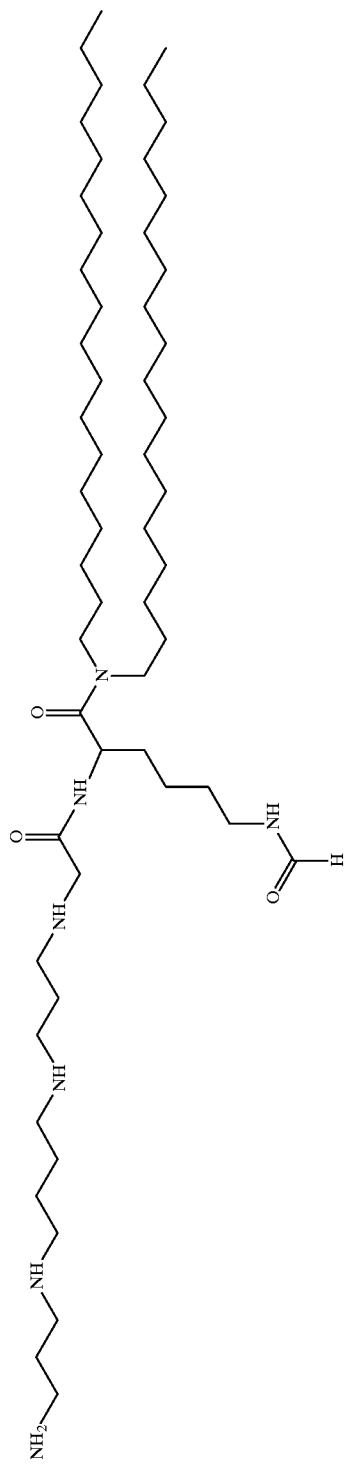
(24) RPR122760A
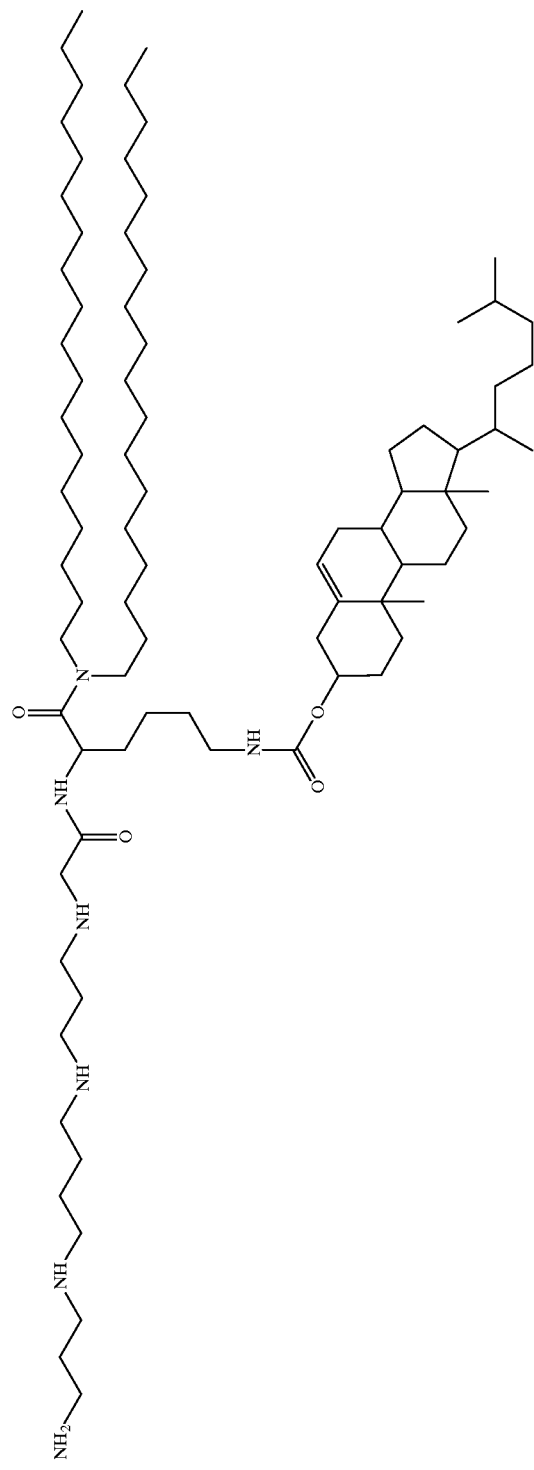
(25) RPR128142a

-continued
(26)
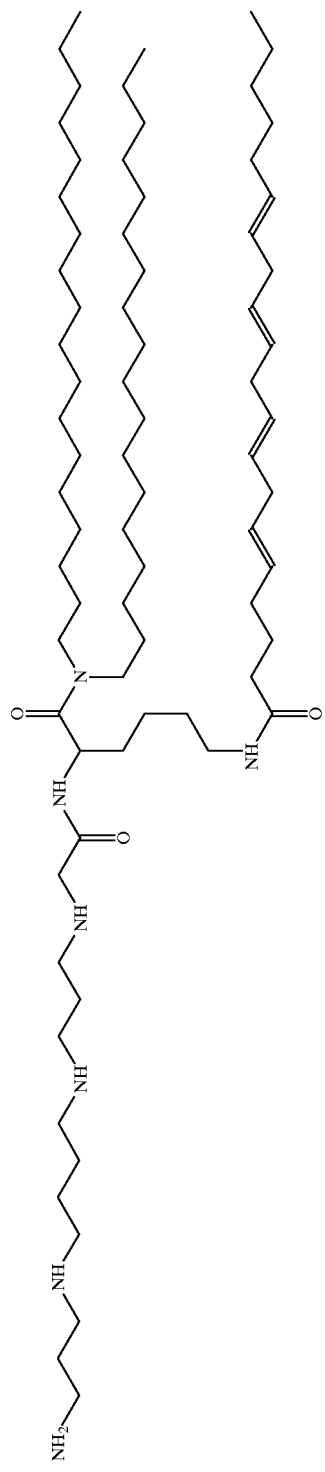
RPR130605
(28)
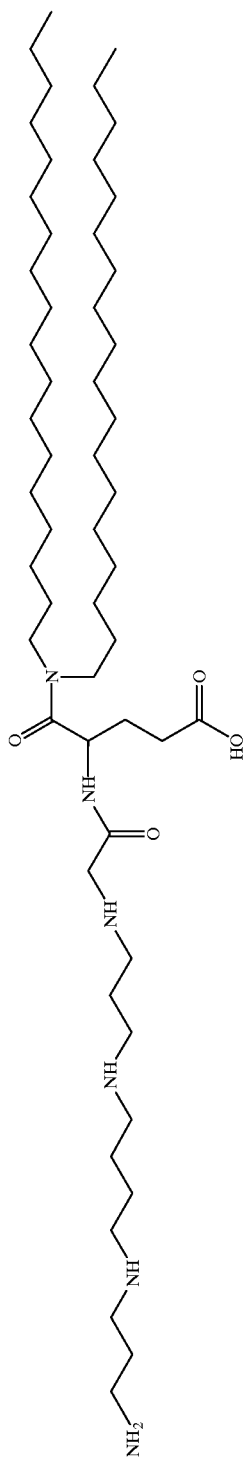
RPR126097

-continued
(29)
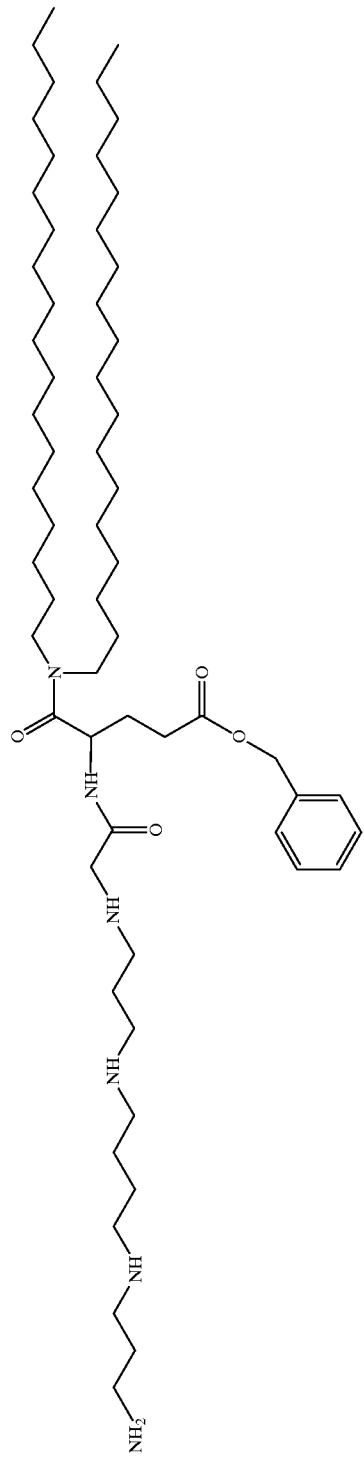
RPR123027a
(31)
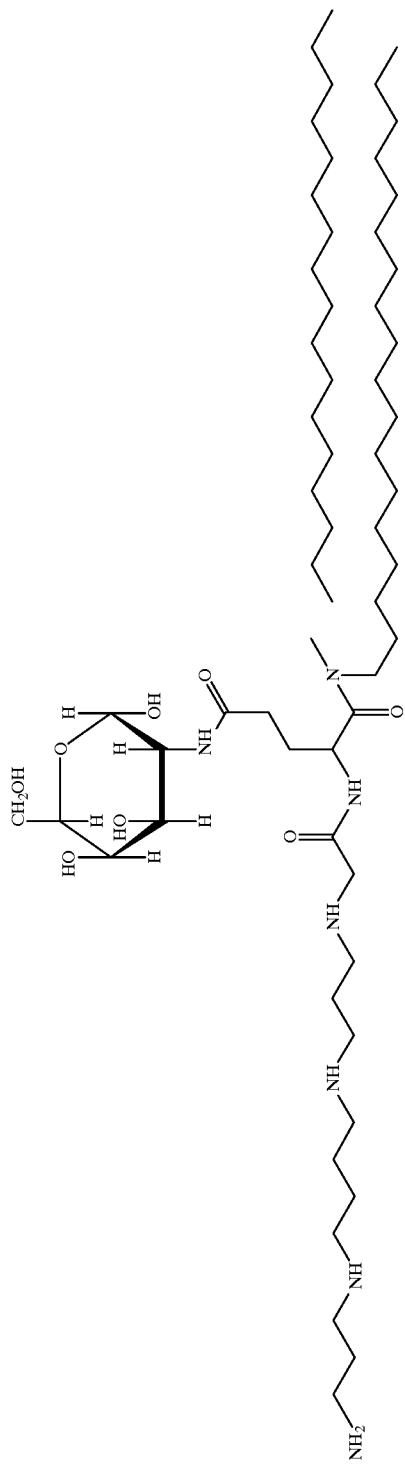
RPR130596a

-continued
(32)
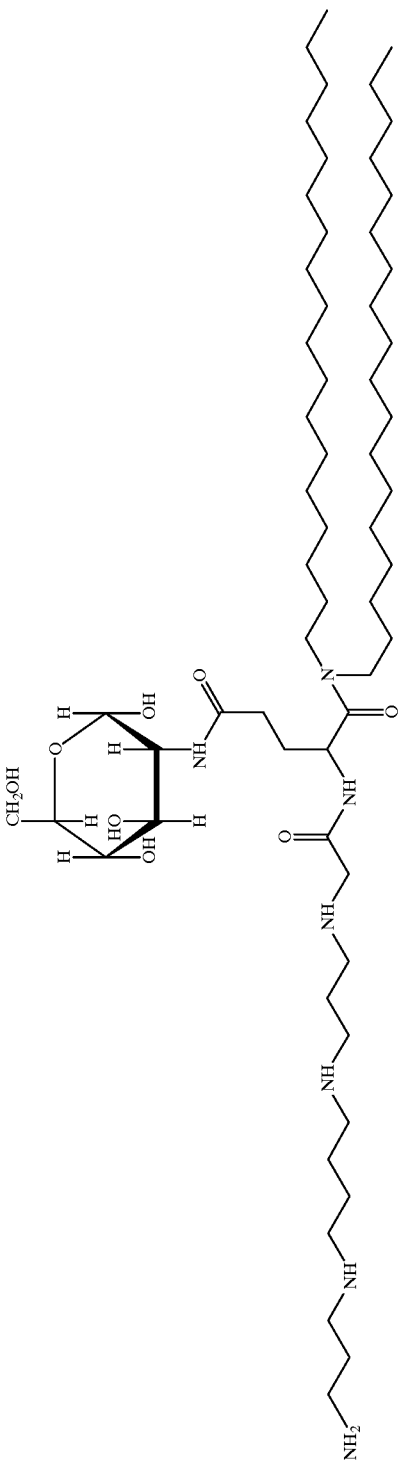
RPR130595A
(33)
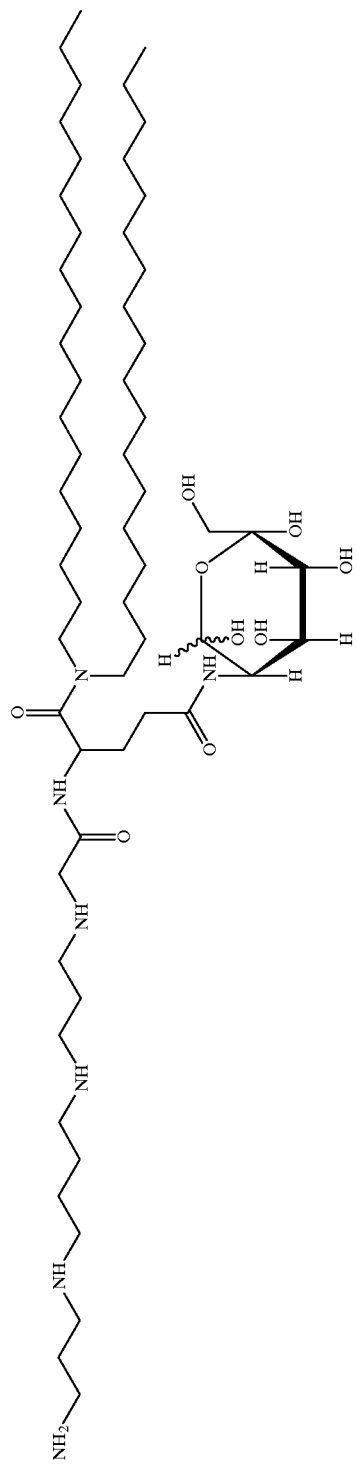
RPR130598A

-continued
(34) 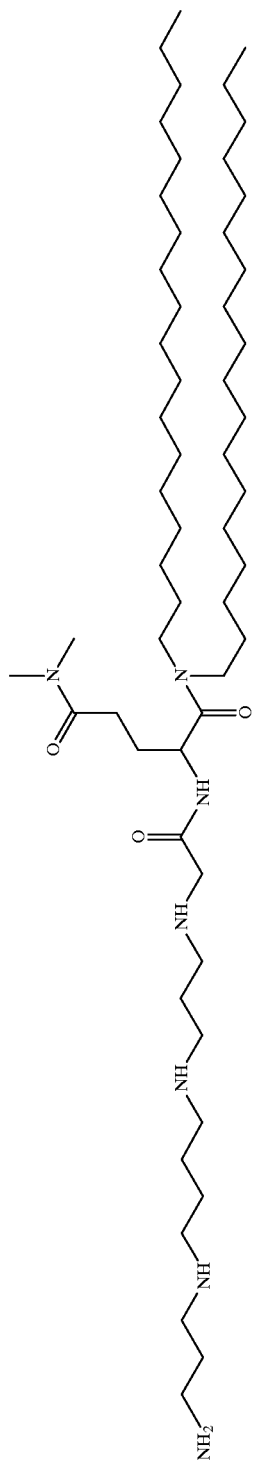 RPR131111a
(35) 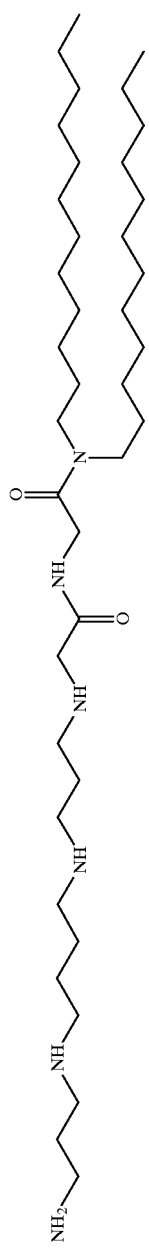 RPR122767a
(36) 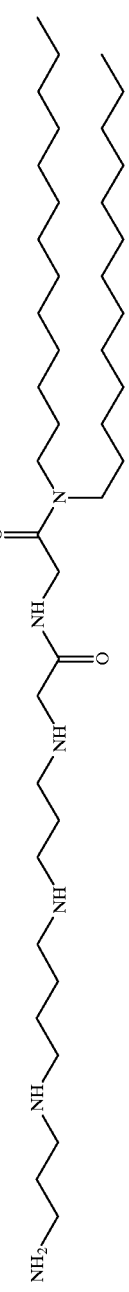 RPR122774a
(37) 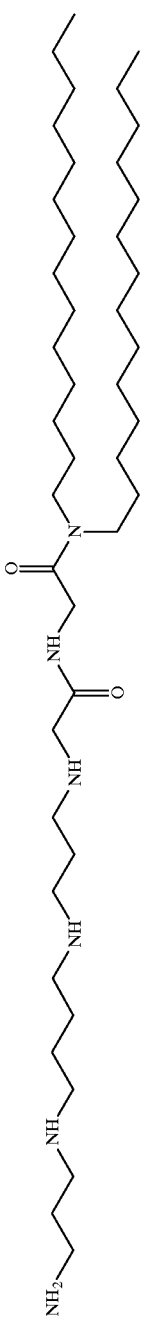 RPR122766a -continued
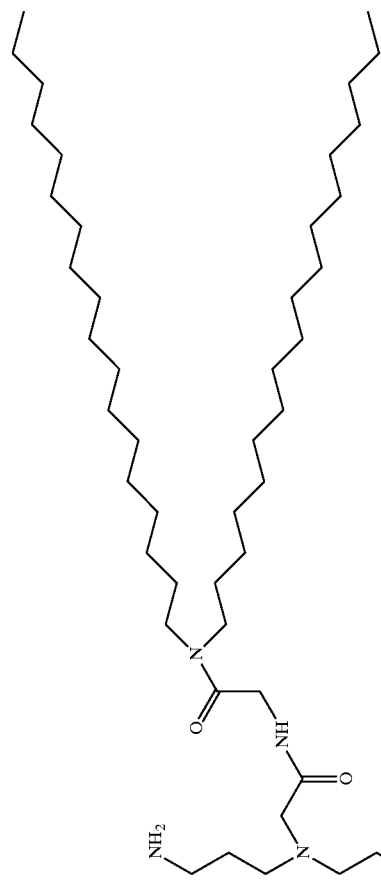
(39) RPR126096a
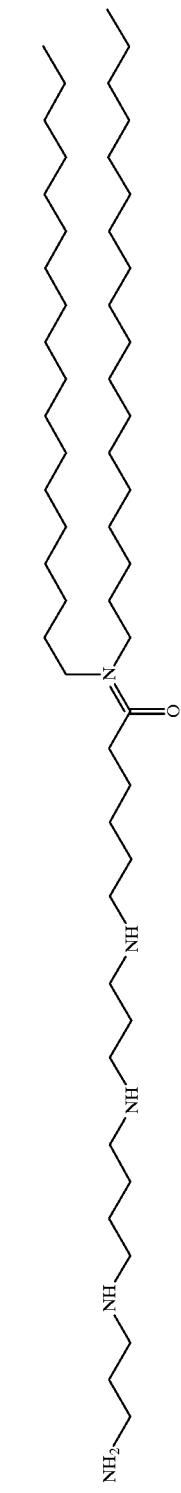
(41) RPR122786
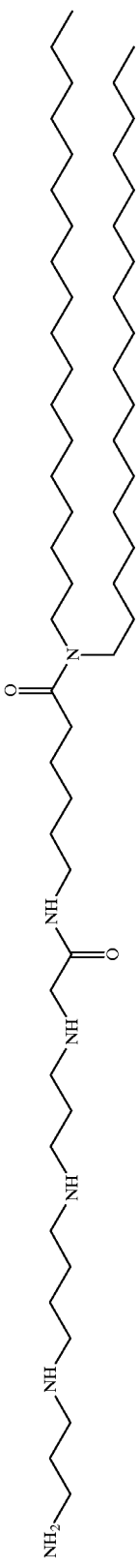
(42) RPR128506a An original solid-phase methodology for preparing asyzmmetric functionalized polyamines from which the lipopolyamines according to the invention are derived has also been developed within the Context of the present invention.

Access to asymmetric functionalized polyamines is conventionally limited by the need for selective introduction of modifications into linear or branched symmetric polyamines. The chemical differences between the primary and secondary amine groups of a polyamine require great selectivity in order to carry out reactions such as alkylations, Michael-type additions or acylations. Furthermore, the selectivity imposed by such chemical differences is not compatible with a selective alkylation in a group of several primary and secondary amines, as is encountered in polyamines. The conventional response to such restrictions is to construct asymmetric functionalized polyamines from monomer blocks bearing, on the one hand, an amine group capable of being "polyaminated" and, on the other hand, the appropriately protected asymmetric function. This approach thus requires a tiresome multistep synthetic strategy and in particular independent protection of the functional groups.

The method developed within the context of the present invention has precisely the aim of getting rid of the drawbacks hitherto encountered with this type of synthesis. Its marked advantage is to lead conveniently and rapidly to polyamines which are selectively functionalized on a single primary amine group by alkylation or reductive alkylation of symmetric polyamines.

The principle of the process claimed is based on the use of a method of solid-phase synthesis to promote a bimolecular reaction between the alkylating reagent and the polyamine, thereby avoiding polyalkylation of the latter. More precisely, the present invention relates to a process characterized in that it uses the coupling of at least one lipid fraction to at least one asymmetric polyamine fraction, the said polyamine fraction having been obtained beforehand by a bimolecular reaction between an alkylating agent covalently attached to a solid support and a symmetric polyamine. According to this approach, the alkylating reagent is covalently attached to a polymeric support by esterification or amidation. The symmetric polyamine reacts with the alkylating agent in the solid phase by a bimolecular reaction which leads to the mono-functionalized asymmetric polyamine attached to the support. The free amines of the product are usually protected in the solid phase with protecting groups BOC or Z type and, lastly, the products are cleaved from the solid-phase support. These polyamino acids are, as is convenient, coupled to the lipid fractions to give the desired transfecting agents. For this coupling, it is possible to use common peptide coupling agents such as BOP, Pybop, BopCl and DCC, for example. The methodology also makes it possible to assemble the entire transfecting agent on the solid support with the possible introduction of tracer peptides, sugars or fluorescent probes into the molecules. Of course, it turns out to be possible to carry out this type of grafting on the free lipopolyamine.

The feasibility of the method was demonstrated by the synthesis of several linear or branched, asymmetric and functionalized polyamino acids.

The subject of the present invention is also any therapeutic application of lipopolyamines as described above, either directly or in pharmaceutical compositions.

As explained above, the compounds of general formula I prove to be most particularly advantageous for the in vitro and in vivo transfection of nucleic acids. They efficiently compact DNA and are advantageously of greatly reduced toxicity.

In order to obtain a maximum effect for the compositions of the invention, the respective proportions of the compound of general formula I and of the nucleic acid are preferably determined such that the ratio R of positive charges in the lipopolyamine considered to negative charges in the said nucleic acid is optimal. Since this optimal ratio varies in particular according to the mode of use, namely in vivo or in vitro, and according to the cell type to be transfected, it is optimized for each particular case. This optimization falls within the competence of a person skilled in the art.

In the pharmaceutical compositions of the present invention, the polynucleotide may be either a deoxyribonucleic acid or a ribonucleic acid. It may be sequences of natural or artificial origin, and in particular genomic DNA, cDNA, mRNA, tRNA, rRNA, hybrid sequences or synthetic or semi-synthetic sequences of modified or unmodified oligonucleotides. These nucleic acids may be of human, animal, plant, bacterial, viral etc. origin. They may be obtained by any technique known to those skilled in the art, and in particular by the screening of banks, by chemical synthesis or by mixed methods including the chemical or enzymatic modification of sequences obtained by the screening of banks. They may moreover be incorporated into vectors, such as plasmid vectors.

As regards more particularly the deoxyribonucleic acids, they may be single- or double-stranded, as well as short oligonucleotides or longer sequences. These deoxyribonucleic acids may bear therapeutic genes, sequences for regulating transcription or replication, modified or unmodified antisense sequences, regions for binding to other cell components, etc.

For the purposes of the invention, the term therapeutic gene is understood in particular to refer to any gene which codes for a protein product having a therapeutic effect. The protein product thus encoded may be a protein, a peptide, etc. This protein product may be homologous with respect to the target cell (that is to say a product which is normally expressed in the target cell when the latter exhibits no pathology). In this case, the expression of a protein makes it possible, for example, to overcome an insufficient expression in the cell or the expression of a protein which is inactive or weakly active on account of a modification, or alternatively of overexpressing the said protein. The therapeutic gene may thus code for a mutant of a cell protein, having increased stability, modified activity, etc. The protein product may also be heterologous with respect to the target cell. In this case, an expressed protein may, for example, make up or provide an activity which is deficient in the cell, enabling it to combat a pathology or to stimulate an immune response.

Among the therapeutic products, in the sense of the present invention, which may more particularly be mentioned are enzymes, blood derivatives, hormones, lymphokines, interleukins, interferons, TNF, etc. (FR 92/03120), growth factors, neurotransmitters or their precursors or synthetic enzymes, trophic factors: BDNF, CNTF, NGF, IGF, GMF, aFGF, bFGF, NT3, NT5, HARP/pleotrophin, etc., dystrophin or a minidystrophin (FR 9111947), the CFTR protein associated with mucoviscidosis, tumour-suppressant genes: p53, Rb, RapIA, DCC, k-rev, etc. (FR 93/04745), genes coding for factors involved in coagulation: factors VII, VIII, IX, genes involved in DNA repair, suicide genes (thymidine kinase, cytosine deaminase), haemoglobin genes or genes of other transport proteins, genes corresponding to the proteins involved in the metabolism of lipids, of apolipoprotein type, chosen from apolipoproteins A-I, A-II, A-IV, B, C-I, C-II, C-III, D, E, F, G, H, J and apo(a), metabolic enzymes such as, for example, lipoprotein lipase, hepatic lipase, lecithin cholesterol acyltransferase, 7 alpha-cholesterol hydroxylase, phosphatitic acid phosphatase, or alternatively lipid transfer proteins such as cholesterol ester transfer protein and phospholipid transfer protein, an EDL binding protein or alternatively a receptor chosen, for example, from LDL receptors, chylomicron-remnant receptors and scavenger receptors, etc.

The therapeutic nucleic acid may also be an antisense sequence or a gene whose expression in the target cell makes it possible to control the expression of genes or the transcription of cellular mRNA. Such sequences may, for example, be transcribed in the target cell into complementary RNA of cellular mRNA and thus block their translation into protein, according to the technique described in patent EP 140,308. The therapeutic genes also comprise the sequences coding for ribozymes which are capable of selectively destroying target RNAs (EP 321,201).

As indicated above, the nucleic acid may also contain one or more genes coding for an antigenic peptide, capable of generating an immune response in humans or animals. In this particular embodiment, the invention thus makes it possible to produce either vaccines or immunotherapeutic treatments applied to humans or to animals, in particular against microorganisms, viruses or cancers. They may in particular be antigenic peptides specific for Epstein Barr virus, for HIV virus, for hepatitis B virus (EP 185,573), for pseudo-rabies virus, for syncytia-forming virus, for other viruses or alternatively specific for tumours (EP 259,212).

Preferably, the nucleic acid also comprises sequences which allow the expression of the therapeutic gene and/or of the gene coding for the antigenic peptide in the desired cell or organ. These may be sequences which are naturally responsible for expression of the gene considered when these sequences are capable of functioning in the infected cell. They may also be sequences of other origin (responsible for the expression of other proteins, or even synthetic). In particular, they may be promoter sequences for eukaryotic or viral genes. For example, they may be promoter sequences derived from the genome of the cell which it is desired to infect. Similarly, they may be promoter sequences derived from the genome of a virus. In this regard, there may for example be mentioned the promoters of genes E1A, MLP, CMV, RSV, etc. In addition, these expression sequences may be modified by addition of activation sequences, regulation sequences, etc. It may also be an inducible or repressible promoter.

Moreover, the nucleic acid may also contain, in particular upstream of the therapeutic gene, a signal sequence which directs the therapeutic product synthesized into the secretion pathways of the target cell. This signal sequence may be the natural signal sequence of the therapeutic product, but it may also be any other functional signal sequence, or an artificial signal sequence. The nucleic acid may also contain a signal sequence which directs the therapeutic product synthesized towards a particular compartment of the cell.

In another embodiment, the present invention relates to compositions comprising a nucleic acid, a lipopolyamine as claimed and an adjuvant capable of associating with the lipopolyamine/nucleic acid complex and of improving the transfecting power thereof. The Applicant has indeed shown that the transfecting power of lipopolyamines may, unexpectedly, be increased in the presence of certain adjuvants (lipids, peptides or proteins for example), capable of associating with the lipopolyamine/nucleic acid complex.

In this respect, the compositions of the invention may comprise one or more neutral lipids as adjuvants. Such compositions are particularly advantageous, especially when the ratio R is low. The Applicant has indeed shown that the addition of a neutral lipid makes it possible to improve the formation of the nucleolipid particles and, surprisingly, to promote the penetration of the particle into the cell by destabilizing its membrane.

More preferably, the neutral lipids used in the context of the present invention are lipids containing 2 fatty chains.

In a particularly advantageous manner, natural or synthetic lipids, which may be zwitterionic or devoid of ionic charge under the physiological conditions, are used. They may be chosen more particularly from dioleoylphosphatidylethanolamine (DOPE), oleoylpalmitoylphosphatidylethanolamine (POPE), di-stearoyl, -palmitoyl, -myristoyl phosphatidylethanolamine as well as derivatives thereof N-methylated 1 to 3 times, phosphatidylglycerols, diacylglycerols, glycosyldiacylglycerols, cerebrosides (such as galactocerebrosides in particular), sphingolipids (such as sphingomyelins in particular) or alternatively asialogangliosides (such as asialoGM1 and GM2 in particular).

These various lipids may be obtained either by synthesis or by extraction from organs (example: the brain) or from eggs, by standard techniques well known to those skilled in the art. In particular, the extraction of natural lipids may be performed using organic solvents (see also Lehninger, Biochemistry).

Very recently, the Applicant has demonstrated that it is also particularly advantageous to employ, as adjuvant, a compound which is or is not directly involved in the condensation of the said nucleic acid (WO96/25508).

The presence of such a compound in a transfecting composition based on a lipopolyamine makes it possible to reduce the amount of this agent considerably, with the ensuing beneficial consequences in terms of toxicology, without having any negative impact on the transfecting activity of the said composition. On the contrary, this composition advantageously has a higher level of transfection.

The expression "compound involved in the condensation of the nucleic acid" is understood to define a compound which directly or indirectly compacts the nucleic acid. More precisely, this compound may act directly on the nucleic acid to be transfected or may act on an associated compound which itself is directly involved in the condensation of this nucleic acid. Preferably, it acts directly on the nucleic acid.

According to a preferred embodiment, this agent acting on the condensation of the nucleic acids consists, partly or totally, of peptide units (KTPKKAKKP)-(SEQ ID No. 1) and/or (ATPAKKAA)-(SEQ ID No. 2), it being possible for the number of units to range between 2 and 10. In the structure of the compound according to the invention, these units may be repeated continuously or non-continuously. Thus, they may be separated by biochemical linkages, for example one or more amino acids, or by chemical bonds. Such an agent may also be partly or totally derived from a histone, from a nucleoline, from a protamine and/or from one of the derivatives thereof.

Preferably, the compositions of the invention comprise from 0.01 to 20 equivalents of adjuvant per one equivalent of nucleic acids on a weight/weight basis and, more preferably, from 0.5 to 5.

The compositions according to the invention may be formulated for the purpose of topical, cutaneous, oral, rectal, vaginal, parenteral, intranasal, intravenous, intramuscular, subcutaneous, intraoccular, transdermal, etc. administration. The pharmaceutical compositions of the invention preferably contain a vehicle which is pharmaceutically acceptable for an injectable formulation, in particular for direct injection into the desired organ, or for topical administration (to skin and/or mucous membrane). They may in particular be sterile, isotonic solutions or dry compositions, in particular freeze-dried compositions, which, by addition depending on the case of sterilized water or of physiological saline, allow injectable solutions to be made up. The doses of nucleic acid used for the injection and the number of administrations may be adapted according to various parameters, and in particular according to the mode of administration used, the pathology concerned, the gene to be expressed, or alternatively the desired duration of the treatment. As regards more particularly the mode of administration, this may be either a direct injection into the tissues or the circulatory pathways, or a treatment of cells in culture followed by their reimplantation in vivo, by injection or graft.

The present invention thus provides a particularly advantageous method for the treatment of diseases, comprising the in vivo or in vitro administration of a nucleic acid capable of correcting the said disease, in combination with a compound of general formula I under the conditions defined above. More particularly, this method may be applied to diseases resulting from a deficiency of a protein or nucleic acid product and the nucleic acid administered codes for the said protein product or contains the said nucleic acid product.

The invention covers any use of a lipopolyamine according to the invention for the in vivo or in vitro transfection of cells.

The present invention will be described more fully using the examples and figures which follow, which should be considered as being non-limiting illustrations.

BRIEF DESCRIPTION OF THE DRAWINGS

FIG. (1): Measurement of the transfection efficacy after treatment of NIH 3T3 cells (mouse embryonic cells—fibroblasts) with different cationic lipids.

FIG. (2): Measurement of the transfection efficacy after treatment of rabbit SMC cells (primary culture of smooth muscle cells from rabbit aorta) with different cationic lipids.

Figure 1:
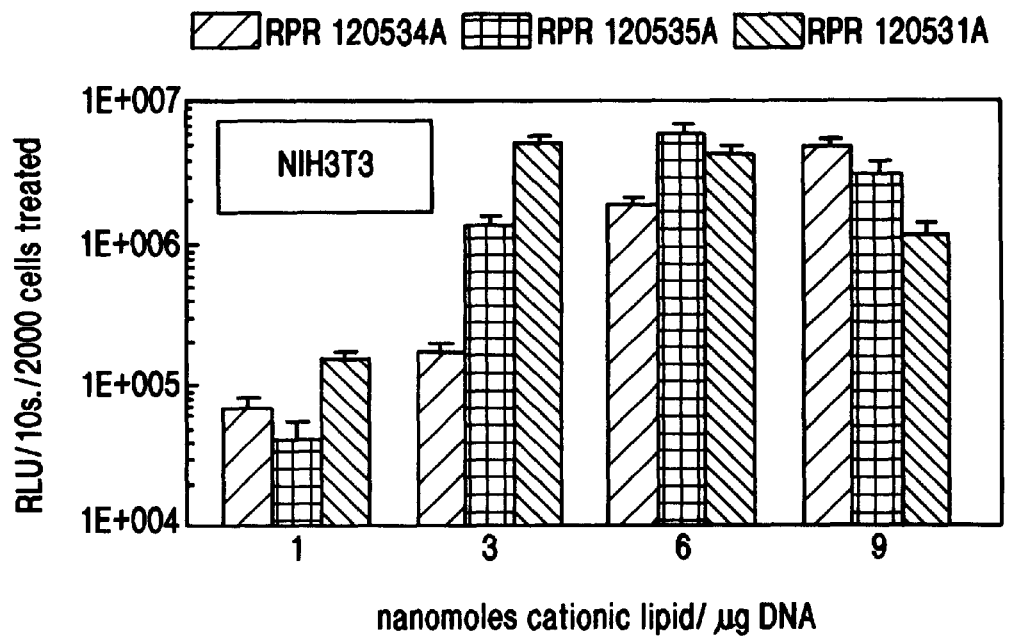
Figure 2:
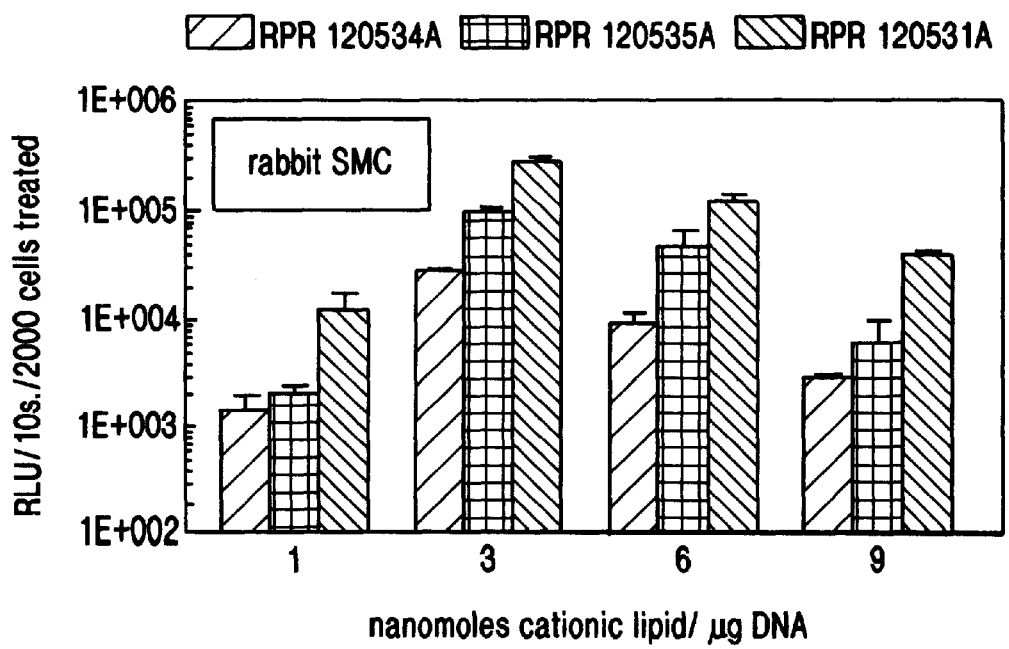
Figure 3:
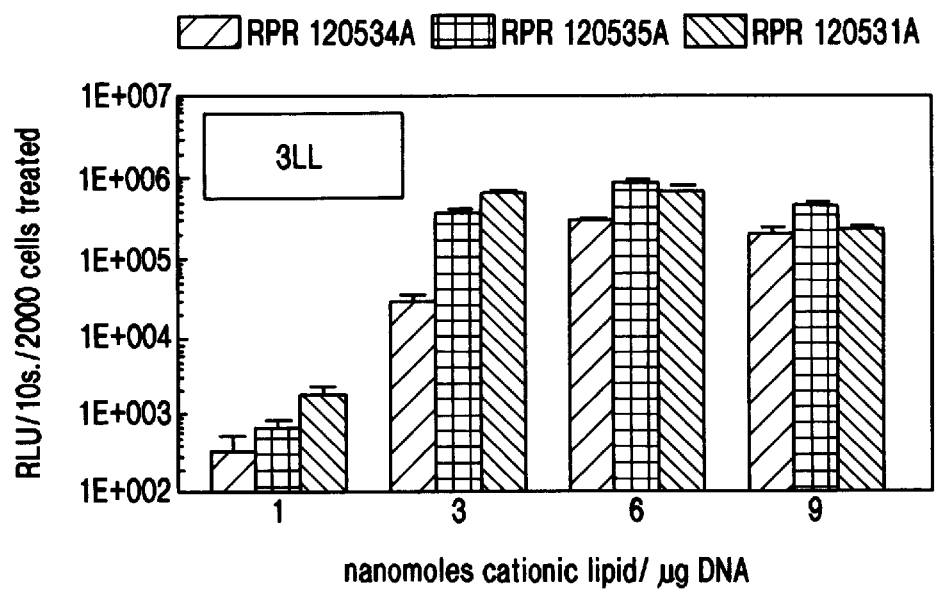
Figure 4:
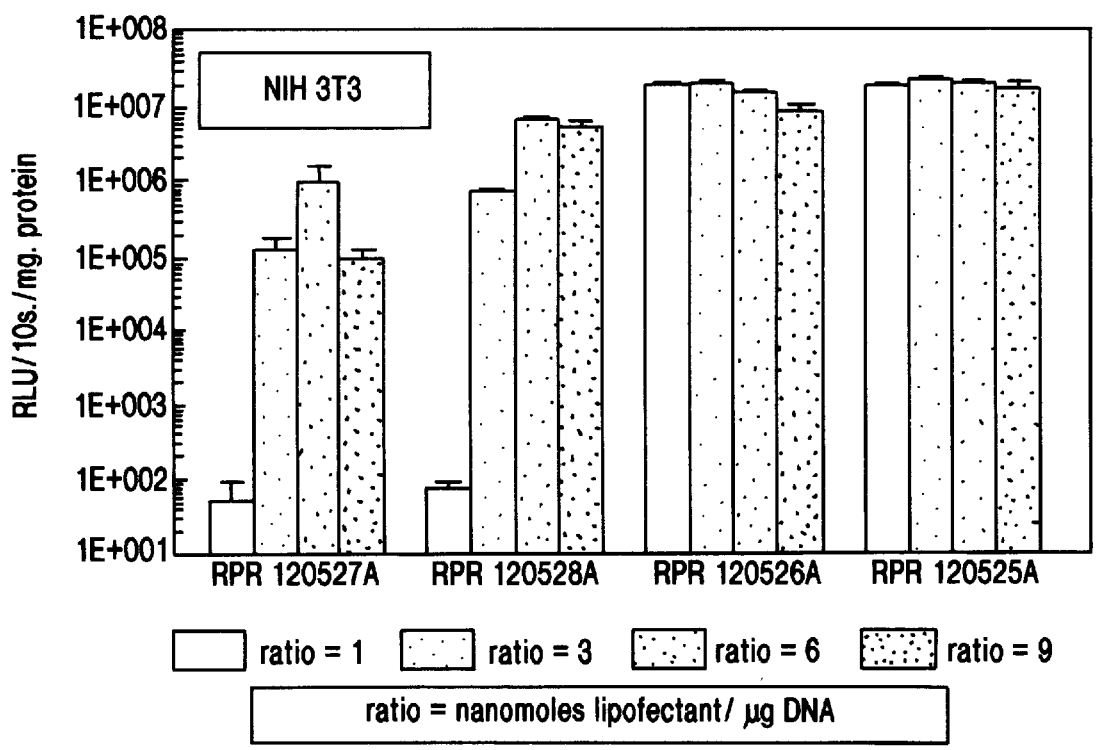

FIG. (3): Measurement of the transfection efficacy after treatment of 3LL cells (Lewis lung carcinoma) with different cationic lipids.

FIG. (4): Measurement of the transfection efficacy after treatment of NIH 3T3 cells (mouse embryonic cells—fibroblasts) with different cationic lipids.

FIG. (5): Effect of the DOPE concentration on the transfection efficacy of 3LL cells.

FIG. (6): Transfection of NIH 3T3 cells with variable amounts of DNA and a constant nanomoles lipofectant/µg of DNA ratio.

ABBREVIATIONS AND SYMBOLS

EtOAc: Ethyl acetate
BOC: t-Butoxycarbonyl
BOP: Benzotriazol-1-yloxytris(dimethylamino)phosphonium hexafluorophosphate
DCC: Dicyclohexylcarbodiimide
DCU: Dicyclohexylurea
DMAP: 4-Dimethylaminopyridine
$DMF_1$: Dimethylformamide
DMSO: Dimethyl sulphoxide
DODA: Dioctadecylamine
PE: Petroleum ether
EtOH: Ethanol
$Et_3N$: Triethylamine
Rf: Coefficient of frontal retention
TFA: Trifluoroacetic acid
THF: Tetrahydrofuran
TMS: Tetramethylsilane
UV: Ultraviolet
SPPS: Solid phase peptide synthesis
HPLC: High pressure liquid chromatography
Z: Benzyloxycarbonyl
ClZ: p-Chlorobenzyloxycarbonyl

A—EQUIPMENT AND METHODS FOR THE CHEMICAL SYNTHESES

1 EQUIPMENT a) Compounds

The starting polyamines are commercially available, for example: spermidine, spermine, tris(2-aminoethyl)amine, phenylenediamine, diamino-ethane (-propane, -butane, -pentane, -hexane, etc.), or may be synthesized by standard methods, for example by exhaustive cyanoethylation of commercially available amines such as diamino-ethane (-propane, -butane,-pentane, -hexane, etc.) amine, spermidine or spermine, to give branched polyamines.

The alkylating agents are chosen, as a function of the method of alkylation, as follows: For a standard alkylation: bromoacetic acid, ω-halocarboxylic acids.

For a reductive alkylation: an ω-aldehyde-carboxylic acid, such as glyoxylic acid, succinic semialdehyde, etc., or a keto acid such as acetoacetic acid or pyruvic acid, etc.

The polymers used are resins which are commercially available for solid-phase peptide synthesis (Merrifield synthesis), for example O-chlorotrityl chloride resin and HMP resin, which give products bearing free acid functions, or a resin of Rink type. The polyamino acids may be synthesized directly on a peptide presynthesized on the solid phase and bearing a bromoalkyl function or an ω-aldehyde acid.

Dioctadecylamine, triethylamine, trifluoroacetic acid, BOP, DMAP and benzyl chloroformate are commercial products, obtained from Aldrich. The NaCl and $NaHCO_3$ solutions are saturated; the $KHSO_4$ solution is 0.5 M.

b) Physical Measurements

The proton NMR spectra were recorded on Bruker 400 and 600 MHz spectrometers.

The mass spectra were acquired on an API-MS/III machine.

c) Chromatographic Techniques

The HPLC analyses are performed on a Merck-Hitachi machine equipped with an AS-2000A autosampler, an L-6200A intelligent pump and an L-4000 UV-visible detector with adjustable wavelength set at 220 nm for analytical separations and at 235 nm for preparative separations. The columns for the analytical separations are BU-300 aquapore Butyl 7 m, 300 A 300×4.6 mm columns from Perkin-Elmer and for the preparative separations are Biosil C18 HL 90–10 250×10 mm columns from Biorad. The mobile phases are $H_2O$ (0.1% TFA) and acetonitrile (0.1% TFA). The flow rate for the analytical analyses is adjusted to 1 ml/min, and, for the preparative analyses, to 4 ml/min.

The thin layer chromatographies (TLC) were carried out on Merck silica gel plates 0.2 mm in thickness.

The column chromatographies were carried out on Merck 60 silica gel of particle size 0.063–0.200 mm. They are revealed either with UV (254 nm), with ninhydrin, by spraying (light spray) an ethanolic solution of ninhydrin (40 mg/100 ml EtOH) to reveal the amines or amides by heating to 150° C., with fluorescamine, by spraying a solution (40 mg/100 ml acetone) to reveal the primary amines, or with iodine, by covering the plate with iodine powder.

The column chromatographies were carried out on Merck 60 silica gel of particle size 0.063–0.200 mm.

d) SPPS Technique of Solid-phase Synthesis

The solid-phase synthesis is performed in a handmade SPPS peptide synthesis manual reactor and the stirrer is a Flask Shaker model A5-6021. The progress in the coupling of the polyamines to the solid phase and the progress in the protection of the polyamines in the SPPS is monitored by the Kaiser test [Kaiser, E., Colescolt, D. L., Bossinger, C. D. and Cook, P. I. *Anal. Biochem.* 34(2), 595 (1970)]. The resin used in the examples for the SPPS is chlorotrityl chloride resin from Novabiochem-Suisse.

2—GENERAL PROCEDURE a)—Synthesis of Symmetric Polyamines Illustrated by the Preparation of (N,N,N',N'-tetraaminopropyl)-1,4-diaminobutane:

147 g of 1,4-diaminobutane and 1000 ml of demineralized water are loaded into a 2-liter three-necked round-bottomed flask. The solution is stirred magnetically. 443 g of acrylonitrile are added over 1 hour via a pressure-equalized dropping funnel, the temperature being maintained at 38° C. A reflux condenser is then mounted on the flask and the reaction mass is maintained at 80° C. on a water bath for 1 hour. The fluorescamine test proves to be negative and the excess acrylonitrile is evaporated off under vacuum at 40° C.

Two phases are obtained. The lower organic phase is separated out, washed with 300 ml of water and transferred into a 1000 ml round-bottomed flask. 170 ml of a water/methanol mixture (1:1 v/v) are added. The resulting mixture is left to crystallize overnight. The following day, the crystals are filtered off on a 500 ml sinter funnel of porosity 3.

The filter cake on the sinter funnel is washed with methanol (2×170 ml) and ether (2×150 ml). The product is dried on a dish in a desiccator under vacuum (26 mm) overnight. 461 g of product are thus obtained (93% yield). The product was analysed by NMR and MS and the analyses are in agreement. The product is hydrogenated without further purification.

30 g of the above polynitrile (0.1 mol) are loaded into a 1-liter stainless steel autoclave. A solution of 140 ml of ethanol (95%) and 8 g of NaOH (0.2 mol) is prepared at the same time in a beaker. When the sodium hydroxide has dissolved, this solution is loaded into the autoclave. Nitrogen is passed into the autoclave and 8 ml of Raney nickel on charcoal are loaded in. The autoclave is closed. The initial hydrogenation pressure is 52 atm and it falls to 28.5 atm over 5 hours at room temperature. The suspension is filtered on paper, the filter is washed with ethanol (2×25 ml) and the filtrates are concentrated to dryness under vacuum. The oil is mixed with 30 ml of water and extracted with 100 ml of $CH_2Cl_2$. The organic phase is dried over $MgSO_4$, filtered and then evaporated under vacuum. A yellowish fluid oil is obtained (27 g, 85% yield).

The product was analysed by TLC (single spot), NMR and MS and the analyses were in agreement. The product is used without further purification.

b)—Method A: Anchoring of an Acidic Function to the Polymeric Support:

Chlorotrityl chloride resin (5 g, 1.2 mmol Cl/g resin) is loaded into an SPPS reactor, 50 ml of $CH_2Cl_2$ are added and the mixture is stirred for 5 min. Bromoacetic acid (1.05 g, 7 mmol) is added, followed by DIEA (0.95 ml, 7.5 mmol). The reactor is stirred for two hours at room temperature. The liquid is filtered and the resin is washed with $CH_2Cl_2$ and iPrOH (10×50 ml) and MeOH (2×50 ml). Lastly, the resin is dried under a stream of nitrogen.

c)—Method B: Reaction of the Polyamines with the Bromoacetyl Resin:

The polyamine (10 molar excess) is dissolved in 50 ml of $CH_2Cl_2$ and loaded into a reactor containing the product obtained by method A. The reactor is stirred for 2 h at room temperature. The solvent is filtered and the resin is washed with $CH_2Cl_2$ and iPrOH (10×50 m); the Kaiser test is positive.

d)—Protection of the Polyamino Acids on the Resin:
Method C:

Di-tert-butyl dicarbonate (48 mmol) and DIEA (50 mmol) are dissolved in $CH_2Cl_2$ (50 ml) and loaded into a reactor containing the product obtained according to method B. The reactor is stirred overnight. The following day, the Kaiser test is negative. The solvent is filtered and the resin is washed alternately with $CH_2Cl_2$ and iPrOH (10×50 ml), MeOH (2×50 ml) and ether (2×50 ml). The resin is dried under a stream of nitrogen. The Kaiser test is still negative.
Method D:

The resin obtained by method B (1.5 g) is loaded into a round-bottomed flask and $CH_2Cl_2$ (20 ml) is added, followed by DIEA (20 mmol). The mixture is stirred magnetically and benzyl chloroformate (14 mmol) is added dropwise over 5 min. The pH is maintained at 11 by addition of DIEA. The following day, the resin is passed into an SPPS reactor, filtered and washed alternately with $CH_2Cl_2$ and iPrOH (10×20 ml) and ether (2×20 ml). The resin is dried under a stream of nitrogen.

e)—Method E: Cleavage of the Protected Polyamino Acids from the Resin:

The resins obtained by methods C and D are loaded into a 250 ml round-bottomed flask equipped with a magnetic stirrer-bar. A solution composed of 50 ml of $CH_2Cl_2$ and 25 ml of $CF_3CH_2OH$ is added and the mixture is stirred for 2 h. The solution is filtered, the resin is washed with $CH_2Cl_2$ (2×10 ml) and the organic phases thus obtained are combined and evaporated under vacuum. The products are then purified by flash chromatography on $SiO_2$ with $CHCl_3$/MeOH (9:1) as eluent. The fractions containing the products are identified by TLC. (For further details see the examples below).

f)—Method F: Coupling of the Amino Acids with Dilipidylamines:

Boc-amino acid (10 mmol) and C12–C22 dilipidylamine (10 mmol) are loaded into a 250 ml round-bottomed flask. $CHCl_3$ (100 ml) is added and the mixture is stirred until dissolution is complete. TEA (30 mmol) and BOP (33 mmol) are then added. The pH is maintained at 10 with TEA and the reaction is stirred for 2 h. When the reaction is complete (TLC), the chloroform is evaporated off and the solid is taken up in ethyl acetate (300 ml). The organic phase is washed with $KHSO_4$ (4×100 ml), $NaHCO_3$ (4×100 ml), and NaCl (4×100 ml). The organic phase is dried over $MgSO_{41}$, filtered and evaporated under vacuum. The products are analysed by TLC, NMR and MS and are used without further purification. The yields are about 90%.

g)—Coupling of the Protected Polyamino Acids with Dilipidyl Acid Amides and Cleavage of the Boc and Z Protecting Groups Method G The product obtained by method F (9 mmol) is loaded into a round-bottomed flask equipped with a magnetic stirrer-bar and cold (4° C.) TFA (30 ml) is added. The solution is stirred for 1 h. The TFA is evaporated off under vacuum. The product is dissolved by addition of DMF (70 ml). TEA (30 mmol) is added, followed by the protected polyamino acid obtained by method E (9 mmol). The pH is adjusted to 10 and BOP (33 mmol) is added. The solution is stirred for 2 h and monitored by TLC. When the coupling is complete (TLC), $KHSO_4$ solution is added (700 ml) and the product is extracted with ethyl acetate (3×100 ml). The organic phase is washed with $KHSO_4$ (3×50 ml), $NaHCO_3$ (3×50 ml) and NaCl (3×50 ml), dried over $MgSO_4$, filtered and evaporated under vacuum. The products are analysed by NMR, TLC and MS and are deprotected without prior purification. TFA (50 ml) is added to the product and the solution is stirred for 1.5 h, then the TFA is evaporated off. If the product still contains Z or ClZ groups which are not cleavable with TFA, method H is followed directly. The final products are purified by semi-preparative HPLC (see examples).

Method H

The products obtained by method G containing Z or ClZ groups are loaded into a round-bottomed flask equipped with a magnetic stirrer-bar and are dissolved in 10 ml of MeOH/g of product. Pd/C (10%, 1 g/g of product) and ammonium formate (1 g/g of product) are added at room temperature. The hydrogenation is monitored by HPLC. After 2 h the reaction is complete, the mixture is filtered and the filter is washed with 10 ml of MeOH. Double-distilled water is added and the solution is frozen and freeze-dried. The final products are purified by preparative HPLC.

h)—Method I for Deprotection of the Boc Protecting Groups

Trifluoroacetic acid (50 ml) is added to the product containing the Boc groups (1 mmol) in a round-bottomed flask. The solution is stirred for 1.5 h and the TFA is evaporated off. The amine is completely deprotected and ready for use in the couplings without further purification.

B—EQUIPMENT AND METHOD FOR THE BIOLOGICAL STUDY

1. PLASMIDS USED FOR THE IN VITRO TRANSFER OF GENES

The plasmid pCMV-LUC is a construction derived either from the plasmid pGL2-basic vector (Promega) or from the plasmid pGL2-control vector (Promega) by insertion of an Mlu I-Hind III fragment containing the human cytomegalovirus (CMV) promoter extracted from the pcDNA3 vector plasmid (Invitrogen).

2. PROCEDURE FOR PREPARATION OF THE SOLUTIONS USED FOR THE TRANSFECTION

The products described in the invention are dissolved to a concentration of 20 mM in ethanol or in water, and are then diluted in water, taking care to ensure that the final ethanolic concentration is less than 10%.

The nucleic acid solutions diluted in physiological saline (0.15M NaCl) are added to the lipofectant solutions in a 1/1 (v/v) ratio. After vortex homogenization and incubation for 15 minutes at room temperature, the DNA/lipofectant solutions are distributed, at a final concentration of 9% (v/v), into wells in which the cells have been washed with protein-free growth medium (serum) and taken up in growth medium containing or free of serum.

C—EQUIPMENT FOR THE IN VIVO TESTS

1. EQUIPMENT a) Experimental Models:

6 adult (>8 weeks) female C57/BL mice tumours of type 3LL (Lewis lung carcinoma) obtained by passing tumour fragments from animal to animal, implanted on the flank under the skin.

b) Plasmids Used:

pXL 2622: this is derived from pGL2 basic (Promega) in which the cytomegalovirus (CMV) promoter extracted from pCDNA3 (Invitrogen) has been inserted upstream of the gene coding for luciferase. This plasmid is obtained by the technique of precipitation with PEG (Ausubel) and is stored in 10 mM Tris 1 mM EDTA pH 8 at 4° C. at a concentration of about 10 μg of DNA per μl.

2. PROCEDURES

Solutions injected: the DNA to be transfected is first dissolved in the buffer, the peptide $(KTPKKAKKP)_2$ SEQ ID No. 1 is then added and, after 20 minutes, a solution of cationic lipids at high concentration (20 or 40 mM) is added to the mixture. After addition of all the products, the mixture contains, besides the DNA (at a final concentration of 0.5 mg/ml), the peptide (0.75 mg/ml) and the cationic lipid, 150 mM NaCl, 5% D-glucose and 5 mM MES pH 6.2. The injection is carried out 20 to 30 minutes after the solution has been prepared.

EXAMPLE 1

Synthesis of $H_2(CH_2)_3NH(CH_2)_4NH(CH_2)_3$ $NHCH_2COGlyN[-(CH_2)_{17}CH_3]_2$ (6)

a—Synthesis of {Boc-[3-(Boc-{4-[Boc-(3-Boc-aminopropyl)amino]butyl}amino)propyl]amino}acetic acid (3)

The resin obtained according to method A is reacted with spermine according to methods B, C and E. The protected product is purified by chromatography on $SiO_2$. The yield is 40%.

TLC: $R_f$=0.32 ($CHCl_3$/MeOH, 9:1); HPLC, $R_t$=4.22 min ($H_2O$/MeCN: 3 min [40/60], 3–20 min [0/100], 35 min [0/100]; $^1$H NMR spectrum (400 MHz, $(CD_3)_2SO-d_6$ with addition of a few drops of $CD_3COOD-d_4$, δ in ppm): 1.40 (4 s, 36H: $C(CH_3)_3$); 1.46 (mt, 4H: central $CH_2CH_2$ of butyl); 1.64 and 1.74 (2 mts, 2H each: central $CH_2$ of the propyls); 2.96 (t, J=7 Hz, 2H: $CH_2NCOO$); 3.15 (mt, 8H: $CH_2NCH_2$); 3.23 (t, J=7.5 Hz, 2H: $CH_2NCOO$); 3.83 (s, 2H: $OCONCH_2COO$); $MH^+$: 661.

b—Synthesis of {Z-[3-(Z-{4-[Z-(3-Z-aminopropyl)-amino]butyl}amino)propyl]amino}acetic acid (4)

The resin obtained according to method A is reacted with spermine according to methods B, C and D. The protected product is purified by chromatography on $SiO_2$. The yield is about 20%.

TLC: $R_f$=0.85 ($CHCl_3$/MeOH, 8:2); HPLC, $R_t$=6.92 min ($H_2O$/MeCN: 3 min [40/60], 3–20 min [0/100], 35 min [0/100]; $^1$H NMR spectrum (400 MHz, $(CD_3)_2SO-d_6$, at a temperature of 413 K, δ in ppm): 1.49 (mt, 4H: central $CH_2CH_2$ of the butyl); 1.74 and 1.81 (2 mts, 2H each: central $CH_2$ of the propyls); 3.07 (q, J=7 Hz, 2H: $CH_2NCOObenzyl$); from 3.15 to 3.30 (mt, 8H: $CH_2NCH_2$); 3.33 (t, J=7.5 Hz, 2H: $NCH_2COO$); 3.70 (s, 2H: $OCONCH_2COO$); 5.07–5.10–5.12 and 5.13 (4s, 2H each: $ArCH_2OCON$); 6.65 (unres. mult., 1H: NHCO); from 7.25 to 7.40 (mt, 20H: aromatic H); $MH^+$: 797.

c—Boc-Gly-dioctadecylamide. (5)

Boc-Gly is coupled to dioctadecylamine according to method F; 90% yield.

TLC: $R_f$=0.9 (CHCl$_3$/MeOH, 9:1); MH$^+$=679; $^1$H NMR spectrum (300 MHz, CDCl$_3$, δ in ppm): 0.89 (t, J=7 Hz, 6H: CH$_3$); 1.29 (mt, 60H: central CH$_2$ of the fatty chains); 1.49 (s, 9H: C(CH$_3$)$_3$); 1.55 (mt, 4H: 1 CH$_2$ of each fatty chain); 3.15 and 3.33 (2t, J=7.5 Hz, 2H each: NCH$_2$ of the fatty chains); 3.95 (d, J=5 Hz, 2H: OCONCH$_2$CON); 5.57 (unres. mult., 1H: CONH).

d—H$_2$N(CH$_2$)$_3$NH(CH$_2$)$_4$NH(CH$_2$)$_3$NHCH$_2$COGlyN[(CH$_2$)$_{18}$]$_2$ (6)

Products (3) and (5) or (4) and (5) are coupled according to method G. The products are deprotected as described in method G for the Boc-protected product and method H for the Z-protected product. The product is purified by semi-preparative HPLC and the fractions are analysed by HPLC.

HPLC, $R_t$=15.35 min, (H$_2$O/MeCN: 3 min [40/60], 3–20 min [0/100], 35 min [0/100]; BYK 2 053$^1$H NMR spectrum (400 MHz, (CD$_3$)$_2$SO-d$_6$ with addition of a few drops of CD$_3$COOD-d$_4$, at a temperature of 300 K, δ in ppm): 0.83 (t, J=7 Hz, 6H: CH$_3$); 1.23 (mt, 60H: central CH$_2$ of the fatty chains); 1.43 and 1.53 (2 mts, 2H each: 1 CH$_2$ of each fatty chain); 1.63 (mt, 4H: central CH$_2$CH$_2$ of the butyl); 1.96 (mt, 4H: central CH$_2$ of the propyls); 2.93–3.00 and 3.22 (3 mts, 16H in total: NCH$_2$); 3.83 (s, 2H: NCH$_2$CON); 4.03 (s, 2H: CONCH$_2$CON); MH$^+$=821.

EXAMPLE 2

Synthesis of H$_2$N(CH$_2$)$_3$NH(CH$_2$)$_4$NH(CH$_2$)$_3$NHCH$_2$CON[(CH$_2$)$_{18}$]$_2$ (7).

Product (3) is coupled with dioctadecylamine according to method F and deprotected according to method G. The product is purified by semi-preparative HPLC and the fractions are analysed by HPLC.

HPLC, $R_t$=15.2 min, (H$_2$O/MeCN: 3 min [40/60], 3–20 min [0/100], 35 min [0/100]; $^1$H NMR spectrum (400 MHz, in a mixture of ⅔ CF$_3$COOD and ⅓ CD$_3$COOD-d$_4$δ in ppm): 0.78 (t, J=7 Hz, 6H: CH$_3$); 1.20 (mt, 60H: central CH$_2$ of the fatty chains); 1.52 (mt, 4H: 1 CH$_2$ of each fatty chain); 1.80 (mt, 4H: central CH$_2$CH$_2$ of the butyl); 2.23 and 2.32 (2 mts, 2H each: central CH$_2$ of the propyls); from 3.10 to 3.40 (3 mts, 16H in total: NCH$_2$); 4.15 (s, 2H: NCH$_2$CON); MH$^+$=764.

EXAMPLE 3

Synthesis of H$_2$N(CH$_2$)$_3$NH (CH$_2$)$_4$NH—(CH$_2$)$_3$NHCH$_2$COArgN[(CH$_2$)$_{18}$]$_2$ (9)

a—Boc-Arg(Z$_2$)dioctadecylamide (8).

The product is synthesized by coupling of BocArg(Z$_2$) and dioctadecylamine by method F, in a yield of 91%.

TLC, Rf =0.9 (CHCl$_3$/MeOH, 9:1); MH$^+$=1046.

b—H$_2$N(CH$_2$)$_3$NH(CH$_2$)$_4$NH(CH$_2$)$_3$NHCH$_2$COArgN[(CH$_2$)$_{18}$]$_2$ (9)

The product (3) or (4) is coupled with product (8) by method G and deprotected by method G (Boc) and/or H (Z). The final product is purified by semi-preparative HPLC and the fractions are analysed by analytical HPLC.

HPLC, $R_t$=13.83 min, (H$_2$O/MeCN: 3 min [40/60], 3–20 min [0/100], 35 min [0/100]; $^1$H NMR spectrum (400 MHz, (CD$_3$)$_2$SO—d$_6$, δ in ppm): 0.90 (t, J=7 Hz, 6H: CH$_3$); 1.28 (mt, 60H: CH$_2$ of the fatty chains); from 1.40 to 1.80 (mt, 12H: CH$_2$); 1.93 (mt, 4H: central CH$_2$ of the propyls); from 2.80 to 3.10 (mt, 16H: NCH$_2$ and NCH$_2$ of the fatty chains); 3.42 (mt, 2H: CH$_2$N of the amido); 3.77 (mt, 2H: NCH$_2$CON); 4.67 (mt, 1H: NCHCON); from 6.80 to 7.50 (broad unres. mult., 2H: NH$_2$); 7.78–7.92–8.80 and 9.03 (mt and 3 unres. mults. respectively, 1H–2H–4H and 1H respectively: CONH—NH and NH$_2$); MH$^+$: 920.

EXAMPLE 4

Synthesis of H$_2$N(CH$_2$)$_3$NH(CH$_2$)$_4$NH (CH$_2$)$_3$NHCH$_2$COArg—(Z)$_2$N[(CH$_2$)$_{17}$—CH$_3$]$_2$ (10)

Product (3) is coupled to product (8) by method G and the Boc groups are cleaved by the same method. The product is purified by semi-preparative HPLC and the fractions are analysed by analytical HPLC.

HPLC, $R_t$=17.75 min, (H$_2$O/MeCN: 3 min [40/60], 3–20 min [0/100], 35 min [0/100]; $^1$H MMR spectrum (400 MHz, (CD$_3$)$_2$SO, δ in ppm): 0.87 (t, J=7 Hz, 6H: CH$_3$); 1.25 (mt, 60H: central CH$_2$ of the fatty chains); 1.40 and 1.57 (2 mts, 2H each: 1 CH$_2$ of each fatty chain); 1.65 (mt, 8H: central CH$_2$CH$_2$ of the butyls); 1.95 (mt, 4H: central CH$_2$ of the propyls); from 2.85 to 3.05 (mt, 14H in total: NCH$_2$); 3.23 (t, J=7.5 Hz, 2H: NCH$_2$); 3.75 (s, 2H: NCH$_2$CON); 3.85 and 3.95 (2 mts, 1H each: CH$_2$NC); 4.67 (mt, 1H: CONCHCON); 5.07 and 5.25 (limiting AB and s respectively, J=13.5 Hz, 2H each: NCOOCH$_2$Ar); from 7.25 to 7.45 (mt, 10H: aromatic H); 7.95–8.85–9.00 and 9.20 (4 unres. mults.: exchangeable H); MH$^+$: 1188.

EXAMPLE 5

Synthesis of H$_2$N (CH$_2$)$_3$NH (CH$_2$)$_4$NH(CH$_2$)$_3$NHCH$_2$COLys-(rhodamine)N[(CH$_2$)$_{17}$—CH$_3$]$_2$ (13)

a—Boc-Lys(Z)dioctadecylamide (11)

The product was synthesized by coupling of BocLys(ClZ) with dioctadecylamine by method F, in a yield of 89%.

TLC, Rf=, 92 (CHCl$_3$/MeOH, 9:1); MH$^+$: 918.

b—BocHN(CH$_2$)$_3$NBoc(CH$_2$)$_4$NBoc(CH$_2$)$_3$NBocCH$_2$COLys-(ClZ)N[(CH$_2$)$_{17}$—CH$_3$]$_2$ (12)

Product (3) is coupled to product (11) by method G (without deprotection of the Boc).

$^1$H NMR spectrum (400 MHz, (CD$_3$)$_2$SO-d$_6$, at a temperature of 423 K, δ in ppm): 0.92 (t, J=6.5 Hz, 6H: CH$_3$); 1.32 (mt, 60H: central CH$_2$ of the fatty chains); 1.44 (2 s, 36H in total: C(CH$_3$)$_3$); from 1.50 to 1.80 (mt, 16H: 1 CH$_2$ of each fatty chain—central CH$_2$CH$_2$ of the butyl —CH$_2$CH$_2$CH$_2$ and central CH$_2$ of the propyl); 3.00 (q, J=6.5 Hz, 2H: OCONCH$_2$); 3.05 (g, J=6.5 Hz, 2H: CH$_2$NCOO); from 3.15 to 3.40 (mt, 14H: NCH$_2$ of fatty chains —CH$_2$NCH$_2$ and CH$_2$NCH$_2$CH$_2$N); 3.80 (s, 2H: OCONCH$_2$CON); 4.75 (mt, 1H: CONCHCON); 5.15 (s, 2H: NCOOCH$_2$Ar); 5.97 and 6.53 (2 mts, 1H each: OCONH and NHCOO); 7.08 (d, J=7.5 Hz, 1H: CONH); from 7.30 to 7.50 (mts, 4H: aromatic H).

c—H$_2$N(HC$_2$)$_3$NH(CH$_2$)$_4$NH(CH$_2$)$_3$NHCH$_2$COLys(rhodamine)-N[(CH$_2$)$_{17}$—CH$_3$]$_2$ (13)

The ClZ group on the lysine of product (12) is cleaved by method H and the product thus obtained is dried under vacuum, taken up in ether and rinsed with NaHCO$_3$ and NaCl. The ether is dried over MgSO$_4$ and evaporated under vacuum.

77 mg (60 μmol) of the deprotected product are dissolved in 3 ml of MeOH, DIEA (64 μl) is added, followed by tetramethylrhodamine isothiocyanate (30 mg, 68 μmol); the solution is stirred for 17 h and the reaction is monitored by TLC. The following day, the solution is concentrated to dryness under vacuum. TFA (4 ml) is then added and the mixture is left stirring for 1 h. The TFA is evaporated off and the crude product is purified by semi-preparative HPLC, with a final yield of 30%.

TLC, Rf=0.05 (MeOH); HPLC(semi-prep.) R$_t$=61.55 min (H$_2$O/MeCN: 3 min [100/0], 3–45 min [0/100], 45–140 min [0/100]; MH$^+$: 1335.

EXAMPLE 6

Synthesis of H$_2$N(CH$_2$)$_3$NH(CH$_2$)$_4$NH(CH$_2$)$_3$ NHCH$_2$COLys-(biotinyl)N[(CH$_2$)$_{17}$—CH$_3$]$_2$ (14)

Product (12) is deprotected by method H (271 mg, 0.21 mmol) and is dissolved in DMF (10 ml). DIEA (0.11 ml) is added, followed by biotin (56.4 mg, 0.23 mmol) and BOP (102 mg, 0.23 mmol); the pH is maintained at 10 (DIEA) and the end of the reaction is confirmed by the fluorescamine test. The product is recovered as described in method F and is deprotected, without further purification, with TFA (5 ml) for 1 h. The TFA is evaporated off and the product is purified by semi-preparative HPLC, in a yield of 50%.

HPLC, R$_t$=13.12 min, (H$_2$O/MeCN: 3 min [40/60], 3–20 min [0/100], 35 min [0/100]; MH$^+$: 1118.

EXAMPLE 7

Synthesis of {(H$_2$N(CH$_2$)$_3$}$_2$N(CH$_2$)$_4$N{(CH$_2$)$_3$ NH$_2$}(CH$_2$)$_3$—NHCH$_2$COGlyN[(CH$_2$)$_{17}$—CH$_3$]$_2$ (16)

a—{BocNM(CH$_2$)$_3$}$_2$N(CH$_2$)$_4$N{(CH$_2$)$_3$NHBoc}(CH$_2$)$_3$ NBocCH$_2$COOH (15)

Product (1) is anchored to the polymer by method B, protected by method C and cleaved from the resin by method E. The product is purified on SiO$_2$ in a yield of 35%.

TLC: R$_f$=0.2 (CHCl$_3$MeOH, 8:2); $^1$H NMR spectrum (400 MHz, (CD$_3$)$_2$SO-d$_6$, with a few drops of CD$_3$COOD-d$_4$, at a temperature of 433 K, δ in ppm): 1.42 (s, 36H: C(CH$_3$)$_3$); 1.56 (mt, 4H: central CH$_2$CH$_2$ of the butyl); from 1.65 and 1.85 (mt, 8H: central CH$_2$ of the propyls); 2.76 (mt, 12H: CH$_2$N(CH$_2$)$_2$); 3.06 (t, J=6.5 Hz, 6H: OCONCH$_2$); 3.29 (mt, 2H: NCH$_2$); 3.86 (s, 2H: OCONCH$_2$COO); MH$^+$=775.

b—{H$_2$N(CH$_2$)$_3$}$_2$N(CH$_2$)$_4$N{(CH$_2$)$_3$NH$_2$}(CH$_2$)$_3$—NHCH$_2$COGlyN[(CH$_2$)$_{17}$—CH$_3$]$_2$ (16)

Product (15) is coupled with product (5) according to method G. The product is deprotected by method G and is purified by semi-preparative HPLC, the fractions are analysed by analytical HPLC and are freeze-dried. 55% yield.

HPLC (semi-prep.): R$_t$=38.72 min (H$_2$O/MeCN, 10 min [100/0], 10–45 min [0/100], 45–140 min [0/100]; $^1$H NMR spectrum (400 MHz, (CD$_3$)$_2$SO-d$_6$, at a temperature of 386 K, δ in ppm): 0.90 (t, J=7 Hz, 6H: CH$_3$); 1.30 (mt, 60H: central CH$_2$ of the fatty chains); 1.55 (mt, 4H: 1 CH$_2$ of each fatty chain); 1.65 (mt, 4H: central CH$_2$CH$_2$ of the butyl); 1.97 (mt, 8H: central CH$_2$ of the propyls); from 2.80 to 3.05–3.06 and 3.28 (mt and 2 t respectively, J=7.5 Hz, 18H–2H and 4H: NCH$_2$); 3.80 (s, 2H: NCH$_2$CON); 4.03 (d, J=5.5 Hz, 2H: CONCH$_2$CON); from 6.00 to 9.00 (broad unres. mult.: NH2 and NH); 8.27 (mt, 1H: CONH). MH$^+$: 935.

EXAMPLE 8

Synthesis of {H$_2$N(CH$_2$)$_3$}$_2$N(CH$_2$)$_4$N{(CH$_2$)$_3$NH$_2$} (CH$_2$)$_3$—NHCH$_2$CON[(CH$_2$)$_{17}$—CH$_3$]$_2$ (17)

This is synthesized as for product (7), using product (15) in place of product (3). The product is purified by semi-preparative HPLC and the fractions are analysed by analytical HPLC and freeze-dried.

HPLC(semi-prep.): R$_t$=38 min (H$_2$O/MeCN, 10 min [100/0], 10–45 min [0/100], 45–140 min [0/100]; $^1$H NMR spectrum (400 MHz, (CD$_3$)$_2$SO-d$_6$, with a few drops of CD$_3$COOD-d4, δ in ppm): 0.88 (t, J=7 Hz, 6H: CH$_3$); 1.29 (mt, 60H: central CH$_2$ of the fatty chains); 1.52 (mt, 4H: 1 CH$_2$ of each fatty chain); 1.68 (mt, 4H: central CH$_2$CH$_2$ of the butyl); from 1.90 to 2.10 (mt, 8H: central CH$_2$ of the propyls); from 2.90 to 2.95 to 3.15–3.18 and 3.15 (t, mt and 2 broad t respectively, J=7.5 Hz, 24H in total: NCH$_2$); 4.02 (s, 2H: NCH$_2$CON); MH$^+$: 878.

EXAMPLE 9

Synthesis of {H$_2$N(CH$_2$)$_2$}$_2$N(CH$_2$)$_2$ NHCH$_2$COGlyN[(CH$_2$)$_{17}$—C$_3$]$_2$ (19)

a—{BocNH(CH$_2$)$_2$}$_2$N(CH$_2$)$_2$NBocCH$_2$COOH (18)

This is synthesized as for product (15), using tris (aminoethyl)amine in place of product (1). 29% yield.

TLC: R$_f$=0.55 (CHCl$_3$/MeOH, 8:2); $^1$H NMR spectrum (400 MHz, (CD$_3$)$_2$SO-d$_6$ at a temperature of 393 K, δ in ppm): 1.44 (s, 27H: C(CH$_3$)$_3$); 2.58 (t, J=6.5 Hz, 4H: CH$_2$NCH$_2$); 2.66 (t, J=7 Hz, 2H: NCH$_2$); 3.04 (q, J=6.5 Hz, 4H: OCONCH$_2$); 3.28 (t, J=7 Hz, 2H: OCONCH$_2$); 3.76 (s, 2H: OCONCH$_2$COO); 6.06 (unres. mult., 2H: CONH); MH$^+$=505.

b—{H$_2$N(CH$_2$)$_2$}$_2$N(CH$_2$)$_2$NHCH$_2$COGlyN[(CH$_2$)$_{17}$—CH$_3$]$_2$) (19)

This is synthesized as for product (17), using product (18) in place of product (15), in a yield of 65%.

HPLC, R$_t$=122 min, (H$_2$O/MeCN, 10 min [100/0], 10–45 min [0/100], 45–140 min [0/100]; $^1$H NMR spectrum (400 MHz, (CD$_3$)$_2$SO-d$_6$, with a few drops of CD$_3$COOD-d4, δ in ppm): 0.87 (t, J=7 Hz, 6H: CH$_3$); from 1.15 to 1.35 (mt, 60H: central CH$_2$ of the fatty chains); 1.45 and 1.55 (2mts, each 2H: 1 CH$_2$ of each fatty chain); 2.64 (t, J=5.5 Hz, 4H: CH$_2$NCH$_2$); 2.75 (t, J=6 Hz, 2H: NCH$_2$); 2.95 (t, J=5.5 Hz, 4H: NCH$_2$); 3.08 (t, J=6 Hz, 2H: NCH$_2$); 3.25 (mt, 4H: NCH$_2$ of the fatty chains); 3.88 (s, 2H: NCH$_2$CON); 4.06 (d, J=5 Hz, 2H: CONCH$_2$CON); 7.75 (residual broad unres. mult.: NH); 8.68 (residual t, J=5 Hz: CONH); MH$^+$: 765.

EXAMPLE 10

Synthesis of {H$_2$N(CH$_2$)$_2$}$_2$N(CH$_2$)$_2$NHCH$_2$CON [(CH$_2$)$_{17}$—CH$_3$]$_2$ (20)

This is synthesized as for product (19), using dioctadecylamine in place of product (5). 73% yield.

HPLC, R$_t$=100.1 min, (H$_2$O/MeCN, 10 min [100/0], 10–45 min [0/100], 45–140 min [0/100]; MH$^+$=708.

EXAMPLE 11

Synthesis of NH$_2$(CH$_2$)$_3$NH(CH$_2$)$_4$NH(CH$_2$)$_3$ NHCH$_2$COLysN[(CH$_2$)$_{17}$CH$_3$]$_2$ (21)

(RPR 127888 A)

Product (12) is deprotected by method H (Cl—Z), followed by method I. The final product is purified by semi-preparative HPLC and the fractions are analysed by analytical HPLC.

HPLC, Rt=11.76 min, (H$_2$O/MeCN: 3 min [60/40], 3–20 min [0/100], 35 min [0/100]; MH$^+$: 892; $^1$H NMR Spectrum (400 MHz, (CD$_3$)$_2$SO-d6, at a temperature of 393 K, d in ppm): 0.91 (t, J=7 Hz, 6H: CH$_3$ of the fatty chains); 1.31 (mt, 60H: (central (CH$_2$)$_{15}$ of the fatty chains); from 1.35 to 1.75 (Mt, 10H: 1 CH$_2$ of each fatty chain, central (CH$_2$)$_3$ of the lysyl); 1.75 (mt, 4H: central (CH$_2$)$_2$ of the butyl); 2.00 (mt, 4H: CH$_2$ of the propyls); 2.82–2.98–3.06 and from 3.10 to 3.50 (2 t—mt and 2 unres. mult. respectively, J=7 Hz, 18H in total: NCH$_2$ of the lysyl —NCH$_2$ of the butyl —NCH$_2$ of the propyls and NCH$_2$ of the fatty chains); 3.62 (s, 2H: NCH$_2$CON); 4.73 (q, J=7 Hz, 1H: CONCHCON of the lysyl); 8.18 (d, J=7 Hz, 1H: CONH of the lysyl).

EXAMPLE 12

Synthesis of NH$_2$(CH$_2$)$_3$NH(CH$_2$)$_4$NH(CH$_2$)$_3$ NHCH$_2$COLys(Cl—Z)N[(CH$_2$)$_{17}$CH$_3$]$_2$ (22)

(RPR 122759 A)

Product (12) is deprotected by method I. The final product is purified by semi-preparative HPLC and the fractions are analysed by analytical HPLC.

HPLC, Rt=16.79 min, (H$_2$O/MeCN: 3 min [60/40], 3–20 min [0/100], 35 min [0/100]; MH$^+$: 1060; $^1$H NMR Spectrum (400 MHz, (CD$_3$)$_2$SO-d$_6$, at a temperature of 373 K, d in ppm): 0.91 (t, J=7 Hz, 6H: CH$_3$ of the fatty chains); 1.31 (mt, 60H: central (CH$_2$)$_{15}$ of the fatty chains); from 1.30 to 1.75 (mt, 10H: 1 CH$_2$ of each fatty chain, central (CH$_2$)$_3$ of the lysyl); 1.72 (mt, 4H: central (CH$_2$)$_2$ of the butyl); 1.95 (mt, 4H: CH$_2$ of the propyls); 2.98–3.06 and from 2.90 to 3.50 (2 mts and unres. mult. respectively, 18H in total: NCH$_2$ of the lysyl —NCH$_2$ of the butyl —NCH$_2$ of the propyls and NCH$_2$ of the fatty chains); 3.59 (s, 2H: NCH$_2$CON); 4.75 (q, J=7 Hz, 1H: CONCHCON of the lysyl); 5.16 (s, 2H: COOCH$_2$Ar); 6.85 (unres. mult., 1H: OCONH); from 7.35 to 7.55 (mt, 5H: aromatic H); 8.15 (unres. mult., 1H: CONH of the lysyl).

EXAMPLE 13

Synthesis of NH$_2$(CH$_2$)$_3$NH(CH$_2$)$_4$NH(CH$_2$)$_3$ NHCH$_2$COLys(CHO)N[(CH$_2$)$_{17}$CH$_3$]$_2$ (24)

(RPR 122760 A) (24).

a—NHBoc(CH$_2$)$_3$NBoc(CH$_2$)$_4$NBoc(CH$_2$)$_3$NBocCH$_2$COLysN-[(CH$_2$)$_{17}$CH$_3$]$_2$ (23).

Product (12) is deprotected by method H (Cl—Z) in a yield of 65%, and is used without further purification.

HPLC, Rt=20.82 min, (H$_2$O/MeCN: 3 min [60/40], 3–20 min [0/100], 35 min [0/100].

b—NH$_2$(CH$_2$)$_3$NH(CH$_2$)$_4$NH(CH$_2$)$_3$NHCH$_2$COLys(CHO)N[(CH$_2$)$_{17}$CH$_3$]$_2$ (24).

Product (23) is coupled with formic acid by method G. The product is purified by semi-preparative HPLC and the fractions are analysed by analytical HPLC.

HPLC, Rt=13.60 min, (H$_2$O/MeCN: 3 min [60/40], 3–20 min [0/100], 35 min [0/100]; MH$^+$: 920; $^1$H NMR Spectrum (400 MHz, (CD$_3$)$_2$SO-d$_6$, at a temperature of 383 K, d in ppm): 0.92 (t, J=7 Hz, 6H: CH$_3$ of the fatty chains); 1.31 (mt, 60H: central (CH$_2$)$_{15}$ of the fatty chains); from 1.35 to 1.70 (mt, 10H: 1 CH$_2$ of each fatty chain, central (CH$_2$)$_3$ of the lysyl); 1.73 (mt, 4H: central (CH$_2$)$_2$ of the butyl); 1.98 (mt, 4H: CH$_2$ of the propyls); from 2.85 to 3.50 (mt, 18H: NCH$_2$ of the lysyl —NCH$_2$ of the butyl —NCH$_2$ of the propyls and NCH$_2$ of the fatty chains); 3.62 (s, 2H: NCH$_2$CON); 4.75 (mt, 1H: CONCHCON of the lysyl); 7.60 (unres. mult., 1H: CONH); 8.05 (broad s, 1H: CH of the aldehyde); 8.18 (unres. mult., 1H: CONH of the lysyl).

EXAMPLE 14

Synthesis of NH$_2$(CH$_2$)$_3$NH(CH$_2$)$_4$NH(CH$_2$)$_3$ NHCH$_2$COLys[Cholesteryl]N [(CH$_2$)$_{17}$CH$_3$]$_2$ (25)

(RPR 128142 A)

Product (23) is coupled with cholesteryl chloroformate according to method G (without use of the BOP reagent). The product is purified by semi-preparative HPLC and the fractions are analysed by analytical HPLC.

HPLC, Rt=21.66 min, (H$_2$O/MeCN: 3 min [60/40], 3–20 min [0/100], 35 min [0/100]; MH$^+$: 1304; $^1$H NMR Spectrum (600 MHz, (CD$_3$)$_2$SO-d$_6$, d in ppm): 0.68 and 0.98 (2 s, 3H each: CH$_3$ at 18 and CH$_3$ at 19 of the cholesteryl); 0.86 (mt, 12H: CH$_3$ of the fatty chains and CH$_3$ at 26 and 27 of the cholesteryl); 0.91 (d, J=7 Hz, 3H: CH$_3$ at 21 of the cholesteryl); 1.31 (mt, 60H: central (CH$_2$)$_{15}$ of the fatty chains); from 0.80 to 2.30 (mt, 42H: 1 CH$_2$ of each fatty chain —CH$_2$ at 1, 2, 4, 7, 11, 12, 15, 16, 22, 23 and 24 of the cholesteryl —CH at 8, 9, 14, 17, 20 and 25 of the cholesteryl —central (CH$_2$)$_3$ of the lysyl and CH$_2$ of the propyls); 1.65 (mt, 4H: central (CH$_2$)$_2$ of the butyl); 2.88 and 2.96 (2 mts, 14H in total: NCH$_2$ of the lysyl —NCH$_2$ of the butyl —NCH$_2$ of the propyls); from 3.20 to 3.50 (mt, 4H: NCH$_2$ of the fatty chains); 3.64 (s, 2H: NCH$_2$CON); 4.23 (mt, 1H: CH at 3 of the cholesteryl); 4.63 (mt, 1H: CONCHCON of the lysyl); 5.30 (mt, 1H: CH at 6 of the cholesteryl); 6.98 (mt, 1H: NHCOO); 7.90 (mt, 1H: CONH of the lysyl); 8.60 to 9.10 (exchangeable unres. mults.).

EXAMPLE 15

Synthesis of NH$_2$ (CH$_2$)$_3$NH(CH$_2$)$_4$NH(CH$_2$)$_3$ NHCH$_2$COLys[Arachidonyl]-N[(CH$_2$)$_{17}$CH$_3$]$_2$ (26)

(RPR 130605)

Product (23) is coupled with arachidonic acid, under a stream of nitrogen and sheltered from the light, according to method G. The product is purified by semi-preparative HPLC and the fractions are analysed by analytical HPLC.

HPLC, Rt=20.67 min, (H$_2$O/MeCN: 3 min [60/40], 3–20 min [0/100], 35 min [0/100]; MH$^+$: 1177; $^1$H NMR Spectrum (400 MHz, (CD$_3$)$_2$SO-d$_6$ with addition of a few drops of CD$_3$COOD-d$_4$, at a temperature of 393 K, d in ppm): 0.90 (t, J=7 Hz, 6H: CH$_3$ of the fatty chains); 0.91 (t, J=7 Hz, 3H: CH$_3$ of the arachidonyl); 1.31 (mt, 60H: central (CH$_2$)$_{15}$ of the fatty chains); from 1.35 to 1.75 (mt, 18H: 1 CH$_2$ of each fatty chain—central (CH$_2$)$_3$ and central CH$_2$ of the arachidonyl and central (CH$_2$)$_3$ of the lysyl); 1.75 (mt, 4H: central (CH$_2$)$_2$ of the butyl); 2.02 (mt, 4H: CH$_2$ of the propyls); 2.10 (mt, 6H: COCH$_2$ and the two =CCH$_2$ of the arachidonyl); 2.80–2.97–3.06 and from 3.10 to 3.50 (mt—t—mt and 2 unres. mults. respectively, J=7 Hz, 24H in total: =CCH$_2$C=of the arachidonyl —NCH$_2$ of the lysyl —NCH$_2$ of the butyl —NCH$_2$ of the propyls and NCH$_2$ of the fatty chains); 3.62 (s, 2H: NCH$_2$CON); 4.73 (dd, J=8 and 5 Hz, 1H: CONCHCON of the lysyl); 5.38 (mt, 8H: CH=CH of the arachidonyl).

EXAMPLE 16

Synthesis of NH$_2$(CH$_2$)$_3$NH(CH$_2$)$_4$NH(CH$_2$)$_3$ NHCH$_2$COGluN[(CH$_2$)$_{17}$CH$_3$]$_2$ (28)

(RPR 126097 A)

a—Boc-Glu(O-Bz)-dioctadecylamine (27)

The product is synthesized by coupling of Boc-Glu(OBz) and dioctadecylamine by method F, in a yield of 90%.

TLC Rf=0.88 (CHCl$_3$/MeOH, 9:1)

b—NH$_2$(CH$_2$)$_3$NH(CH$_2$)$_4$NH(CH$_2$)$_3$NHCH$_2$COGluN[(CH$_2$)$_{17}$CH$_3$]$_2$ (28).

Product (3) or (4) is coupled with product (27) by method G, followed by method H (Cl—Z deprotection). The final product is purified by semi-preparative HPLC and the fractions are analysed by analytical HPLC.

HPLC, Rt=14.64 min, (H$_2$O/MeCN: 3 min [60/40], 3–20 min [0/100], 35 min [0/100]; MH$^+$: 893; $^1$H NMR Spectrum. (400 MHz, (CD$_3$)$_2$SO-d$_6$, at a temperature of 383 K, d in ppm): 0.90 (t, J=7 Hz, 6H: CH$_3$ of the fatty chains); 1.30 (mt, 60H: central (CH$_2$)$_{15}$ of the fatty chains); 1.56 (unres. mult., 4H: 1 CH$_2$ of each fatty chain; from 1.60 to 2.00 (mt, 2H: central CH$_2$ of the glutaryl); 1.73 (mt, 4H: central (CH$_2$)$_2$ of the butyl); 1.98 (mt, 4H: $CH_2$ of the propyls); 2.32 (t, J=7 Hz, 2H: $COCH_2$ of the glutaryl); 3.00–3.06 and 3.45 (t and 2 mts respectively, J=7 Hz, 16H in total: $NCH_2$ of the butyl —$NCH_2$ of the propyls and $NCH_2$ of the fatty chains); 3.65 (broad s, 2H: $NCH_2CON$); 4.85 (mt, 1H: CONCHCON of the glutaryl); 8.19 (broad s, 1H: CONH of the glutaryl).

EXAMPLE 17

Synthesis of $NH_2(CH_2)_3NH(CH_2)_4NH(CH_2)_3$ $NHCH_2COGlu(O-Bz)N[(CH_2)_{17}CH_3]_2$ (29)

(RPR 123027 A)

Product (3) is coupled to product (27) and deprotected by method G (Boc). The final product is purified by semi-preparative HPLC and the fractions are analysed by analytical HPLC.

HPLC, Rt=16.02 min, ($H_2O$/MeCN: 3 min [60/40], 3–20 min [0/100], 35 min [0/100]; $MH^+$: 983; $^1H$ NMR Spectrum (400 MHz, $(CD_3)_2SO-d_6$, at a temperature of 413 K, d in ppm): 0.89 (t, J=7 Hz, 6H: $CH_3$ of the fatty chains); 1.30 (mt, 6OH: central $(CH_2)_{15}$ of the fatty chains); 1.55 (unres. mult., 4H: 1 $CH_2$ of each fatty chain); 1.72 (mt, 4H: central $(CH_2)_2$ of the butyl); from 1.75 to 2.00 (mt, 2H: central $CH_2$ of the glutaryl); 1.99 (mt, 4H: $CH_2$ of the propyls); 2.47 (t, J =7 Hz, 2H: $COCH_2$ of the glutaryl); 2.95–3.05 and 3.40 (3 mts, 16H in total: $NCH_2$ of the butyl —$NCH_2$ of the propyls and $NCH_2$ of the fatty chains); 3.62 (broad s, 2H: $NCH_2CON$); 4.85 (mt, 1H: CONCHCON of the glutaryl); 5.14 (limiting AB, J=12 Hz, 2H: $CH_2$ of the benzyl); 7.35 (mt, 5H: aromatic H of the benzyl); 8.23 (unres. mult., 1H: CONH of the glutaryl).

EXAMPLE 18

Synthesis of $NH_2(CH_2)_3NH(CH_2)_4NH(CH_2)_3$ $NHCH_2COGlu[Galactosamide]—N[(C_2)_{17}CH_3]_2$ (31)

(RPR 130596 A)

a—$BocNH(CH_2)_3NBoc(CH_2)_4NBoc(CH_2)_3NBocCH_2COGluN—[(CH_2)_{17}CH_3]_2$ (30)

Product (3) is coupled to product (27) and the OBz protecting group of the side chain is cleaved off by method H (Cl—Z), and the product is used without further purification.

HPLC, Rt=22.84 min, ($H_2O$/MeCN: 3 min [60/40], 3–20 min [0/100], 35 min [0/100]; $MH^+$: 1293.

b—$NH_2(CH_2)_3NH(CH_2)_4NH(CH_2)_3NHCH_2COGlu$ (Galactosamide)$N-[(CH_2)_{17}CH_3]_2$ (31)

Product (30) is coupled with D-(+)-galactosamine hydrochloride according to method G. The product is purified by semi-preparative HPLC and the fractions are analysed by analytical HPLC.

HPLC, Rt=13.71 min, ($H_2O$/MeCN: 3 min [60/40], 3–20 min [0/100], 35 min [0/100]; $MH^+$: 1054.

EXAMPLE 19

Synthesis of $NH_2(CH_2)_3NH(CH_2)_4NH(CH_2)_3$ $NHCH_2COGlu[Galactosamide]-N[(CH_2)_{17}CH_3]_2$ (32)

(RPR 130595 A)

Product (30) is coupled with D-(+)-glucosamine hydrochloride according to method G. The product is purified by semi-preparative HPLC and the fractions are analysed by analytical HPLC.

HPLC, Rt=12.27 min, ($H_2O$/MeCN: 3 min [60/40], 3–20 min [0/100], 35 min [0/100]; $MH^+$: 1054.

EXAMPLE 20

Synthesis of $NH_2(CH_2)_3NH(CH_2)_4NH(CH_2)_3$ $NHCH_2COGlu[Mannosamide]-N[(CH_2)_{17}CH_3]_2$ (33)

(RPR 130598 A)

Product (30) is coupled with D-(+)-mannosamine hydrochloride according to method G. The product is purified by semi-preparative HPLC and the fractions are analysed by analytical HPLC.

HPLC, Rt=12.98 min, ($H_2O$/MeCN: 3 min [60/40], 3–20 min [0/100], 35 min [0/100]; $MH^+$: 1054.

EXAMPLE 21

Synthesis of $NH_2(CH_2)_3NH(CH_2)_4NH(_2)_3$ $NHCH_2COGlu(N(CH_3)_2N[(CH_2)_{17}CH_3]_2$ (34)

(RPR 131111 A)

Product (30) is coupled with dimethylamine according to method G. The product is purified by semi-preparative HPLC and the fractions are analysed by analytical HPLC.

HPLC, Rt=14.44 min, ($H_2O$/MeCN: 3 min [60/40], 3–20 min [0/100], 35 min [0/100]; $MH^+$: 920; $^1H$ NMR Spectrum (400 MHz, $(CD_3)_2SO-d_6$, d in ppm): 0.89 (t, J=7 Hz, 6H: $CH_3$ of the fatty chains); 1.25 (mt, 60H: central $(CH_2)_{15}$ of the fatty chains); 1.43 and 1.60 (2 mts, 2H each: 1 $CH_2$ of each fatty chain); 1.65 (mt, 4H: central $(CH_2)_2$ of the butyl); 1.65 and from 1.85 to 2.00 (2 mts, 1H each: central $CH_2$ of the glutaryl); 1.95 (mt, 4H: $CH_2$ of the propyls); 2.32 (limiting AB, 2H: $COCH_2$ of the glutaryl); 2.80 and 2.92 (2s, 3H each: $CON(CH_3)_2$); from 2.85 to 3.05 (mt, 12H: $NCH_2$ of the butyl —$NCH_2$ of the propyls); 3.00–3.22–3.45 and 3.58 (4 mts, 1H each: $NCH_2$ of the fatty chains); 3.78 (AB, J=16 Hz, 2H: $NCH_2CON$); 4.75 (mt, 1H: CONCHCON of the glutaryl); 8.72 (d, J=7.5 Hz, 1H: CONH of the glutaryl); 8.85 and from 8.90 to 9.15 (exchangeable unres. mults.).

EXAMPLE 22

Synthesis of $NH_2(CH_2)_3NH(CH_2)_4NH(CH_2)_3$ $NHCH_2COGlyN[(CH_2)_{12}CH_3]_{;2}$ (35)

(RPR 122767 A)

This is synthesized in the same way as product (6), but using didodecylamine in place of dioctadecylamine. The product is purified by semi-preparative HPLC and the fractions are analysed by HPLC.

HPLC, Rt=9.54 min, ($H_2O$/MeCN: 3 min [60/40], 3–20 min [0/100], 35 min [0/100]; $MH^+$: 653; $^1H$ NMR Spectrum (400 MHz, $(CD_3)_2SO-d_6$, at a temperature of 403 K, d in ppm); 0.93 (t, J=7 Hz, 6H: $CH_3$ of the fatty chains); 1.33 (mt, 36H: central $(CH_2)_9$ of the fatty chains); 1.58 (mt, 4H: 1 $CH_2$ of each fatty chain); 1.75 (mt, 4H: central $(CH_2)_2$ of the butyl); 1.95 and 2.00 (2 mts, 2H each: central $CH_2$ of the propyls); 2.98 and 3.00 (2 mts, 12H in total: $NCH_2$ of the butyl and $NCH_2$ of the propyls); 3.30 (t, J=7 Hz, 4H: $NCH_2$ of the fatty chains); 3.58 (s, 2H: $NCH_2CON$); 4.05 (s, 2H: $CONCH_2CON$ of the glycyl).

EXAMPLE 23

Synthesis of $NH_2(CH_2)_3NH(CH_2)_4NH(CH_2)_3$ $NHCH_2COGlyN[(CH_2)_{12}CH_3]_2$ (36)

(RPR 122774 A)

This is synthesized in the same way as product (6), but using ditridecylamine in place of dioctadecylamine. The product is purified by semi-preparative HPLC and the fractions are analysed by HPLC.

HPLC, Rt=10.64 min, ($H_2O$/MeCN: 3 min [60/40], 3–20 min [0/100], 35 min [0/100]; $MH^+$: 681; $^1H$ NMR Spectrum (400 MHz, $(CD_3)_2SO$-$d_6$, at a temperature of 393 K, d in ppm): 0.91 (t, J=7 Hz, 6H: $CH_3$ of the fatty chains); 1.33 (mt, 40H: central $(CH_2)_{10}$ of the fatty chains); 1.58 (mts, 4H: 1 $CH_2$ of each fatty chain); 1.75 (mt, 4H: central $(CH_2)_2$ of the butyl); 2.00 (mt, 4H: central $CH_2$ of the propyls); 2.98 and 3.08 (2 t, J=7 Hz, 12H in total: $NCH_2$ of the butyl and $NCH_2$ of the propyls); 3.32 (t, J=7 Hz, 4H: $NCH_2$ of the fatty chains); 3.65 (s, 2H: $NCH_2CON$); 4.06 (d, J=4 Hz, 2H: $CONCH_2CON$ of the glycyl); 8.60 (broad s, 1H: CONH of the glycyl).

EXAMPLE 24

Synthesis of $NH_2(CH_2)_3NH(CH_2)_4NH(CH_2)_3$ $NHCH_2COGlyN[(CH_2)_{13}CH_3]_2$ (37)

(RPR 122766 A)

This is synthesized in the same way as product (6), but using ditetradecylamine in place of dioctadecylamine. The product is purified by semi-preparative HPLC and the fractions are analysed by HPLC.

HPLC, Rt=9.92 min, ($H_2O$/MeCN: 3 min [60/40], 3–20 min [0/100], 35 min [0/100]; $M^+$: 709; $^1H$ NMR Spectrum (400 MHz, $(CD_3)_2SO$-$d_6$, at a temperature of 393 K, d in ppm): 0.90 (t, J=7 Hz, 6H: $CH_3$ of the fatty chains); 1.31 (mt, 44H: central $(CH_2)_{11}$ of the fatty chains); 1.58 (mt, 4H: 1 $CH_2$ of each fatty chain); 1.76 (mt, 4H: central $(CH_2)_2$ of the butyl); 2.00 (mt, 4H: central $CH_2$ of the propyls); 2.98 and 3.08 (mt and t respectively, J=7 Hz, 12H in total: $NCH_2$ of the butyl and $NCH_2$ of the propyls); 3.30 (t, J=7 Hz, 4H: $NCH_2$ of the fatty chains); 3.65 (s, 2H: $NCH_2CON$); 4.06 (d, J=4 Hz, 2H: $CONCH_2CON$ of the glycyl); 8.10 (unres. mult., 1H: CONH of the glycyl).

EXAMPLE 25

Synthesis of $NH_2(CH_2)_3NH(CH_2)_4N[(CH_2)_3NH_2]$ $CH_2COGlyN[(CH_2)_{17}CH_3]_2$ (39)

(RPR 126096 A)

a—Synthesis of $BocNH(CH_2)_3NBoc(CH_2)_4N[(CH_2)_3NHBoc]CH_2CO_2H$ (38)

During the synthesis of product (3), by-product (38) is recovered during the purification on $Sio_2$.

The yield is 8%. TLC Rf=0.32 ($CHCl_3$/MeOH, 9:1); $MH^+$: 561; $^1H$ NMR Spectrum (400 MHz, $(CD_3)_2SO$-$d_6$, d in ppm): from 1.30 to 1.60 (mt, 4H: central $(CH_2)_2$ of the butyl); 1.40 (s, 27H: $C(CH_3)_3$); 1.56 (mt, 4H: $CH_2$ of the propyls); 2.68 and 3.11 (broad t and t respectively, J=7 Hz, 4H each: $NCH_2$ of the butyl and $NCH_2$ of the propyls); 2.90 and 2.96 (2 q, J=7 Hz, 2H each: $BocNHCH_2$ of the propyls); 3.18 (s, 2H: $NCH_2COO$).

b—$NH_2(CH_2)_3NH(CH_2)_4N[(CH_2)_3NH_2]CH_2COGlyN$ $[(CH_2)_{17}CH_3]_2$ (39)

Products (38) and (5) are coupled according to method G. The product is purified by semi-preparative HPLC and the fractions are analysed by HPLC.

HPLC, Rt=13.60 min, ($H_2O$/MeCN: 3 min [60/40], 3–20 min [0/100], 35 min [0/100]; $MH^+$: 821; $^1H$ NMR Spectrum (400 MHz, $(CD_3)_2SO$-$d_6$ with addition of a few drops of $CD_3COOD$-$d_4$, d in ppm): 0.87 (t, J=7 Hz, 6H: $CH_3$ of the fatty chains); 1.28 (mt, 60H: central $(CH_2)_{15}$ of the fatty chains); 1.46 and 1.54 (2 mts, 2H each: 1 $CH_2$ of each fatty chain); 1.63 (mt, 4H: central $(CH_2)_2$ of the butyl); 1.91 (mt, 4H: $CH_2$ of the propyls); from 2.85 to 3.15 (mt, 12H: $NCH_2$ of the butyl and $NCH_2$ of the propyls); 3.24 (mt, 4H: $NCH_2$ of the fatty chains); 3.76 (unres. mult., 2H: $NCH_2CON$); 4.05 (broad s, 2H: $CONCH_2CON$ of the glycyl).

EXAMPLE 26

Synthesis of $NH_2(CH_2)_3NH(CH_2)_4NH(CH_2)_3NH$ $(CH_2)_3CON[(CH_2)_{17}CH_3]_2$ (41)

(RPR 122786 A)

a—$BocNH(CH_2)_3NBoc(CH_2)_4NBoc(CH_2)_3NBoc(CH_2)_3$ $NBoc (CH_2)_3CO_2H$(40)

Product (40) is synthesized using reductive alkylation on spermine in the presence of $NaCNBH_3$ and succinic semi-aldehyde in solution.

1.8 g of spermine, 60 ml of methanol and 0.138 g of $NaCNBH_3$ are loaded into a 200 ml round-bottomed flask. The solution is placed under vigorous magnetic stirring. A solution of 5.5 ml of succinic semialdehyde (15%) in 30 ml of methanol is run in, via a pressure-equalized dropping funnel, over 100 minutes. Stirring is continued for 100 minutes. The amines are protected with the Boc group as follows: 2.8 ml of TEA are run into the medium, followed by 8.8 g of di-tert-butyl dicarbonate dissolved in 30 ml of methanol. Stirring is continued overnight. The medium is concentrated under vacuum, the product is taken up in ethyl acetate and extracted with three 50 ml fractions of $NaHCO_3$, and the aqueous phases are combined and rinsed with ether (3×100 ml). The pH of the aqueous phase is lowered to 3 with $KHSO_4$, turbidity is observed due to the precipitation of product (41), and the mixture is extracted with ethyl acetate (3×100 ml). The organic phase is dried over $MgSO_4$ and evaporated under vacuum. The product is used without further purification.

b—$NH_2(CH_2)_3NH(CH_2)_4NH(CH_2)_3NH(CH_2)_3CON[(CH_2)_{17}CH_3]_2$ (41)

Product (40) and dioctadecylamine are coupled according to method G. The product is purified by semi-preparative HPLC and the fractions are analysed by HPLC.

HPLC, Rt=15.04 min ($H_2O$/MeCN: 3 min [60/40], 3–20 min [0/100], 35 min [0/100]; $MH^+$: 792; $^1H$ NMR Spectrum (400 MHz, $(CD_3)_2SO$-$d_6$, at a temperature of 383 K, d in ppm): 0.85 (t, J=7 Hz, 6H: $CH_3$ of the fatty chains); 1.22 (mt, 60H: central $(CH_2)_{15}$ of the fatty chains); 1.48 (unres. mult., 4H: 1 $CH_2$ of each fatty chain); 1.72 (mt, 4H: central $(CH_2)_2$ of the butyl); 1.88 (mt, 2H: central $CH_2$ of the aminopentanoyl); 1.99 (mt, 4H: $CH_2$ of the propyls); 2.42 (t, J=7 Hz, 2H: $COCH_2$ of the aminopentanoyl); 2.96–3.03 and 3.22 (3 mts, 18H in total: $NCH_2$ of the aminopentanoyl —$NCH_2$ of the butyl —$NCH_2$ of the propyls and $NCH_2$ of the fatty chains).

EXAMPLE 27

Synthesis of $NH_2(CH_2)_3NH(CH_2)_4NH(CH_2)_3$ $NHCH_2CONH(CH_2)_5CON[(CH_2)_{17}CH_3]_2$ (42)

(RPR 128506 A)

This is synthesized in the same way as product (6), but using Boc-6-aminocaproic acid in place of BocGly. The product is purified by semi-preparative HPLC and the fractions are analysed by HPLC.

HPLC, Rt=13.94 min ($H_2O$/MeCN: 3 min [60/40], 3–20 min [0/100], 35 min [0/100]; $MH^+$: 877; $^1H$ NMR Spectrum (300 MHz, $(CD_3)_2SO$-$d_6$, d in ppm): 0.87 (t, J=7 Hz, 6H: $CH_3$ of the fatty chains); 1.28 (mt, 60H: central $(CH_2)_{15}$ of the fatty chains); 1.48 (mt, 10H: 1 $CH_2$ of each fatty chain and central $(CH_2)_3$ of the aminohexanoyl); 1.65 (mt, 4H: central $(CH_2)_2$ of the butyl); 1.95 (mt, 4H: $CH_2$ of the propyls); 2.27 (t, J=7 Hz, 2H: $COCH_2$ of the aminohexanoyl); from 2.85 to 3.30 (mts, 18H: $NCH_2$ of the aminohexanoyl —$NCH_2$ of the butyl —$NCH_2$ of the propyls and $NCH_2$ of the fatty chains); 3.70 (broad s, 2H: $NCH_2CON$); from 7.90 to 9.10 (exchangeable unres. mults.).

EXAMPLE 28

Synthesis of $NH_2(CH_2)_3NH(CH_2)_4NH(CH_2)_3$
$NHCH_2COGlu(11$-amide-undecanyl,hepta,O acetyl lactose) $N[(CH_2)_{17}CH_3]_2$ (43)
(RPR 130765 A)

Product (30) is coupled with 11-aminoundecanylhepta-O-acetyllactose according to method G. The product is purified by semi-preparative HPLC and the fractions are analysed by analytical HPLC.

HPLC, Rt=15.91 min ($H_2O$/MeCN: 3 min [60/40], 3–20 min [0/100], 35 min [0/100]; MH$^+$: 1680.

EXAMPLE 29

Synthesis of $NH_2(CH_2)_3NH(CH_2)_4NH(CH_2)_3$
$NHCH_2COAsm(\beta-NAc(Ac)_3)N[(CH_2)_{17}CH_3]_2$
(RPR 131283 A) (45)

a-Fmoc-Asm-$\beta$-Glc-NAc(Ac)$_3$-dioctadecylamine (44)

The product is synthesized by coupling of Fmoc-Asm-$\beta$-Glc-NAc(Ac)$_3$—OH and dioctadecylamine by method F.

TLC Rf=0.67 (CHCl$_3$/MeOH, 9:1); HPLC, Rt=25.31 min ($H_2O$/MeCN: 3 min [60/40], 3–20 min [0/100], 35 min [0/100];

b—$NH_2(CH_2)_3NH(CH_2)_4NH(CH_2)_3NHCH_2CO$ Asm ($\beta$-NAc(Ac)$_3$N[(CH$_2$)$_{17}$CH$_3$]$_2$ (45)

Cleavage of the Fmoc group from product (45).

20 ml of DMF and 2 ml of diethylamine are poured onto 0.7 g of product (45). After stirring for 6 hours, the medium is concentrated in vacuo.

The product obtained is coupled with product (3) according to method G. The product is purified by semi-preparative HPLC and the fractions are analysed by analytical HPLC.

HPLC, Rt=15.35 min ($H_2O$/MeCN: 3 min [60/40], 3–20 min [0/100], 35 min [0/100]; MH$^+$: 1207.

EXAMPLE 30

Large-Scale Synthesis in Solution of Product (6)

Product (6) is synthesized by carrying out a reductive alkylation on spermine in the presence of NaCNBH$_3$ and glyoxylic acid in solution.

18.2 g of spermine, 500 ml of methanol and 2 g of NaCNBH$_3$ are loaded into a 2 l round-bottomed flask. The solution is subjected to vigorous magnetic stirring. A solution of 8.45 g of glyoxylic acid in 300 ml of methanol is run in, via a pressure-equalized dropping funnel, over 100 minutes. Stirring is continued overnight. The amines are protected with the Boc group as follows: 14 ml of TEA are run into the medium, followed by 100 g of di-tert-butyl dicarbonate dissolved in 200 ml of THF. Stirring is continued overnight. The medium is concentrated under vacuum and the product is taken up in ethyl acetate (250 ml), rinsed with KHSO$_4$ (6×100 ml) and then with saturated NaCl solution (3×100 ml), dried over MgSO$_4$ and evaporated under vacuum. The product is purified on a column of silica with CHCl$_3$/MeOH (9:1) as eluent. The fractions containing the product are identified by TLC, combined and evaporated under vacuum to give 10 g of product (6) (17% yield for the total synthesis).

The analytical HPLC, mass spectral and NMR analyses are identical to those of the product obtained by the solid-phase method.

EXAMPLE 31

Influence of the (amines/phosphates) Charge Ratio on the Efficacy of (7) RPR 120534A, (6) RPR 120535A and (9) RPR 120531A Transfection Samples of 1×10$^5$ cells [NIH 3T3, 3LL or SMC rabbit] in exponential growth phase on 2 cm$^2$ are treated with lipofectant/pCMV-LUC solutions, having variable charge ratios, for 2 hours at 37° C. under 5% CO$_2$; each sample receives 2 µg of nucleic acid. An investigation of the expression of the reporter gene is carried out after addition of foetal calf serum to a final concentration of 8% followed by incubation for 40 hours in a CO$_2$ oven.

The luciferase activity is assayed by light emission [RLU=relative light unit] in the presence of luciferin, coenzyme A and ATP for 10 seconds and is given relative to 2000 treated cells. The results obtained are reported in FIGS. (1), (2) and (3).

From studying these figures, it emerges clearly that the presence of a glycine in the "spacer" arm between the lipid part and the polyamine makes it possible to obtain a better transfection efficacy for nanomoles cationic lipid/low µg DNA ratios.

EXAMPLE 32

Influence of the (amines/phosphates) Charge Ratio on the Efficacy of (20) RPR 120527A, (19) RPR 120528A, (17) RPR 120526A and (16) RPR 120525A Transfection Samples of 1×10$^5$ NIH 3T3 cells in exponential growth phase on 2 cm$^2$ are treated with lipofectant/pCMV-LUC solutions, having variable charge ratios, for 2 hours at 37° C. under 5% CO$_2$; each sample receives 1 µg of nucleic acid. An investigation of the expression of the reporter gene is carried out after addition of foetal calf serum to a final concentration of 8% followed by incubation for 40 hours in a CO$_2$ oven.

The luciferase activity is assayed in the supernatant obtained after lysis of the cells, by light emission [RLU=relative light unit] for 10 seconds and is given relative to an mg of protein. The results obtained are reported in figure (4). The advantage of the presence of the glycine residue in the "spacer" arm is again demonstrated in this example.

EXAMPLE 33

Influence of the Length of the Spacer Arm on the Transfection Efficacy (6) RPR 120535, (41) RPR 122786 and (42) RPR 128506

Samples of 1×10$^5$ cells [NIH3T3 and HeLa] in exponential growth phase on 2 cm$^2$ are treated with cationic lipid/pCMV-Luc mixtures, having variable concentrations of cationic lipid, at 37° C. in a humid atmosphere under 5% CO$_2$, for 2 hours in the absence of serum proteins. The cell growth medium is then supplemented with foetal calf serum to a final concentration of 8% and the transgenic expression is measured after an additional 40 hours of incubation in a CO2 oven.

The structural characteristics of the spacer arms are as follows:

| RPR No. | Spacer arm |
| --- | --- |
| 122786 | — |
| 120535 | Gly |
| 128506 | $NH_2(CH_2)_5CO$ |

Table I below gives the results obtained, which are expressed for the maximum efficacies obtained with each of the test products.

TABLE I

| | Cationic lipid | HeLa cells | NH3T3 cells |
|---|---|---|---|
| Experiment 1 | RPR120535 (6) | $1.2 \times 10^6 \pm 9.7 \times 10^4$ (4) | $8.7 \times 10^7 \pm 4.5 \times 10^6$ (4) |
| | RPR122786 (41) | $2.3 \times 10^6 \pm 1.6 \times 10^5$ (8) | $4.6 \times 10^7 \pm 5.0 \times 10^6$ (8) |
| Experiment 2 | RPR120535 (6) | $2.4 \times 10^6 \pm 3.2 \times 10^5$ (6) | $7.2 \times 10^7 \pm 8.3 \times 10^6$ (6) |
| | RPR128506 (42) | $1.8 \times 10^6 \pm 1.3 \times 10^5$ (6) | $5.0 \times 10^7 \pm 1.5 \times 10^6$ (6) |

The transfection efficacies are given in RLU/10s/2×103 cells treated. The ratios—nanomoles of lipid/µg of DNA—are indicated in brackets.

Different plasmids were used for Experiments 1 and 2, at a dose of 1 µg and 0.5 µg of DNA/1×105 cells respectively in Experiments 1 and 2.

EXAMPLE 34

Influence of the Structure of the Spacer Arm on the Transfection Efficacy (6) RPR 120535

Under experimental conditions identical to those described in the previous example, but with the introduction of an additional line (3LL cells), we compared the transfection efficacies obtained with the cationic lipid (6) RPR 120535 modified by substitution on the "spacer arm" with an Arg-type, Lys-type or Glu-type group.

The structures of the various spacer arms are as follows:

| RPR No. | SPACER ARM |
|---|---|
| 120531 | Arg |
| 121650 | Arg($Z_2$) |
| 127888 | Lys |
| 122759 | |
| 122760 | |

-continued

| RPR No. | SPACER ARM |
|---|---|
| 128142 | (structure shown) |
| 120535 | Gly |
| 123027 | GluOBz |
| 126097 | Glu |

The transfection efficacies are given in RLU/10s/2×10³ cells treated.

Different plasmids were used for Experiments 1 and 2 at a dose of 0.5 µg and 1 µg of DNA/1×10⁵ cells respectively in Experiments 1 and 2. From the analysis of the results, it emerges that, depending on the cells considered, the presence of a preferably substituted amino acid chain induces a better transfection efficacy.

TABLE II

|  | lipid | HeLa cells | NIH3T3 cells | 3LL cells |
|---|---|---|---|---|
| Experiment 1 | RPR120535 | $1.0 \times 10^6 \pm 1.9 \times 10^5$ | $6.5 \times 10^7 \pm 4.8 \times 10^6$ | |
|  | RPR120531 | $3.7 \times 10^5 \pm 1.0 \times 10^5$ | $1.6 \times 10^7 \pm 2.0 \times 10^6$ | |
|  | RPR121650 | $2.6 \times 10^6 \pm 1.8 \times 10^5$ | $9.1 \times 10^7 \pm 2.7 \times 10^7$ | |
| Experiment 2 | RPR120535 | $2.2 \times 10^6 \pm 3.3 \times 10^5$ | | $1.7 \times 10^6 \pm 1.0 \times 10^5$ |
|  | RPR127888 | $3.1 \times 10^5 \pm 2.9 \times 10^4$ | | $1.4 \times 10^5 \pm 1.7 \times 10^4$ |
|  | RPR122760 | $1.4 \times 10^6 \pm 2.2 \times 10^5$ | | |
|  | RPR122759 | $7.7 \times 10^5 \pm 1.1 \times 10^5$ | | $3.7 \times 10^5 \pm 5.4 \times 10^4$ |
|  | RPR128142 | $6.3 \times 10^6 \pm 6.3 \times 10^5$ | | $9.1 \times 10^4 \pm 9.3 \times 10^3$ |
|  | RPR126097 | $3.6 \times 10^6 \pm 3.6 \times 10^5$ | | $3.0 \times 10^5 \pm 2.3 \times 10^4$ |
|  | RPR123027 | $1.0 \times 10^6 \pm 4.1 \times 10^4$ | | $6.9 \times 10^5 \pm 1.1 \times 10^5$ |

EXAMPLE 34

Influence of the Presence of DOPE in the Lipofectant/DNA Mixture (9) RPR 120531A According to the same procedure as that used in Example 31, DOPE (dioleoylphosphatidylethanolamine) is added to the cationic lipid (9) RPR 120531A in variable molar ratios, before adding DNA to the transfection mixture.

Figure 5:
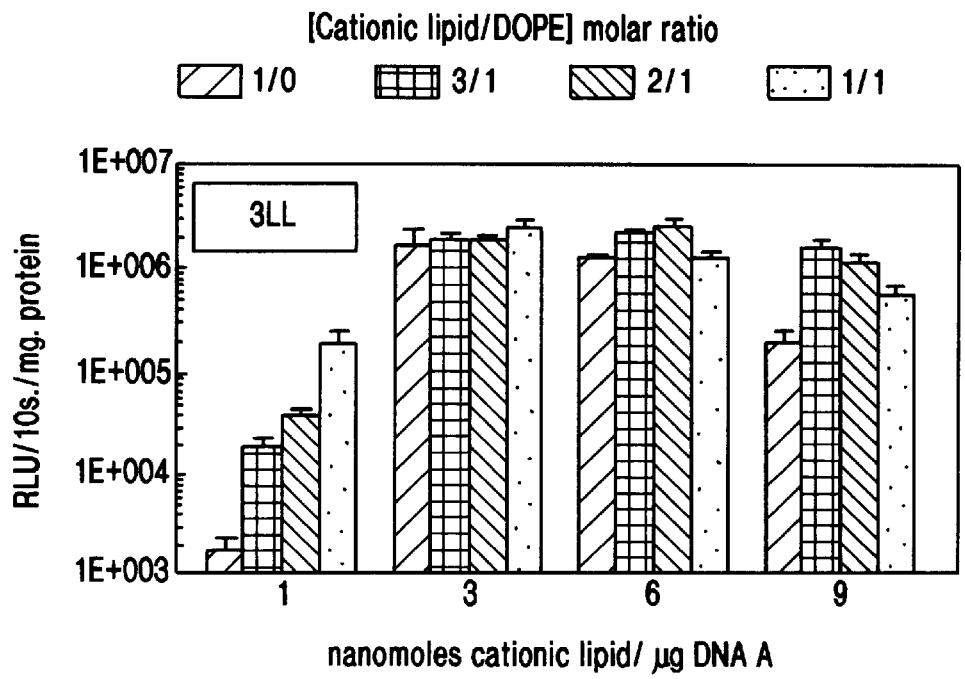

The luciferase activity is assayed in the supernatant after lysis of the cells and is given relative to an mg of protein (FIG. 5).

The presence of DOPE in the lipofectant mixtures makes it possible to improve the transfection efficacy when the concentration of (9) RPR 120531A is low.

EXAMPLE 35

Effect of Serum on the Efficacy of (6) RPR 120535A, (9) RPR 120531A and (10) RPR 121650A Transfection Samples of 1×10⁵ cells [NIH 3T3 or Hela] in exponential growth phase on 2 cm² are treated with lipofectant/pCMV-LUC solutions (3 nanomol lipofectant/µg DNA) in the absence of serum for 2 hours or in the presence of serum in the culture medium. In this example, each sample receives 2 µg of DNA. The expression of luciferase is studied in the supernatant of the cell lysates, expressed as RLU/10s and given relative to an mg of protein. From the analysis of the results, it emerges that the presence of serum has no appreciable effect on the transfection.

EXAMPLE 36

Figure 6:
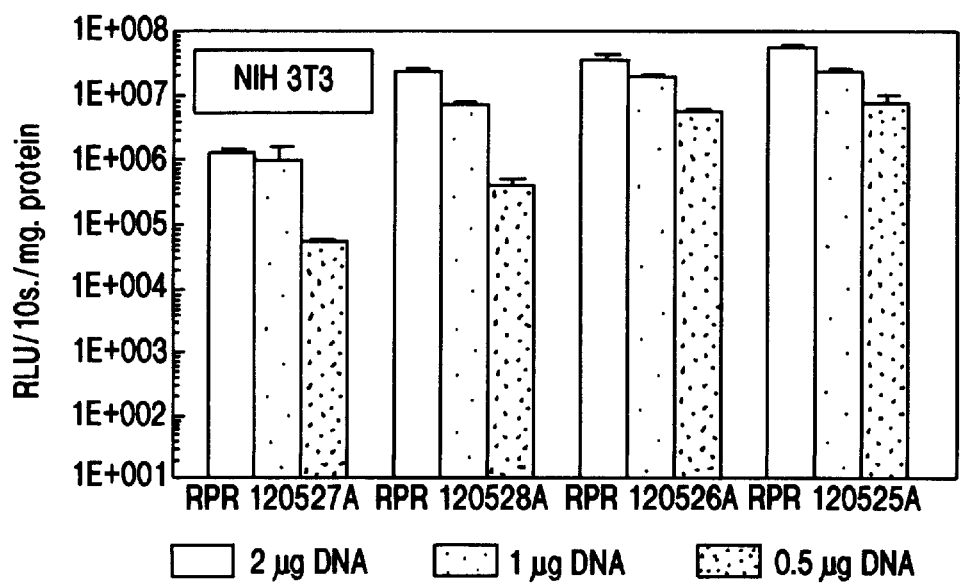

Influence of the Nucleic Acid Concentration in the DNA/lipofectant Mixtures (20) RPR 120527A, (19) RPR 120528A, (17) RPR 120526A and (16) RPR 120525A Under the conditions described in Example 31, samples of NIH 3T3 cells are transfected under conditions in which the nanomoles lipofectant/µg of DNA ratios are optimized—see Example 30—[ratio=6 for (20) RPR 120527A and (19) RPR 120528A—ratio=3 for (17) RPR 120526A and (16) RPR 120525A]. The amounts of DNA provided to each sample range from 0.5 to 2 µg. The results are reported in FIG. 6.

The transfection of 1×10⁵ cells in exponential growth phase with 1 µg of plasmid DNA appears to be a good choice; indeed, the increase in the amount of DNA used leads to an increase in the concentration of cationic lipid in contact with the cells and thus to toxicity problems in certain cases. At a lower DNA concentration, the proportionality with the transfection efficacy is no longer obtained.

EXAMPLE 37

Tests of in Vivo Transfection with Lipopolyamines According to the Invention.

A solution containing a lipopolyamine according to the invention, prepared as described above, is injected into a tumour 7 days after implantation, the mouse being anaesthetized with a ketamine+xylazine mixture. Two days after the injection, tumour tissues are removed, weighed and then chopped up and ground in 500 $\mu$l of lysis buffer (Promega Cell Lysis Buffer E153 A). After centrifugation (20,000 g for 10 minutes), 10 $\mu$l are taken out and used to evaluate the luciferase activity by measuring the total light emission obtained after mixing with 50 $\mu$l of reagent (Promega Luciferase Assay Substrate) in a Lumat LB 9501 luminometer (Berthold), with integration over 10 seconds. The resulting activity is expressed as RLUs (Relative Light Units) estimated for the entire tumour lysis supernatant, or as RLUs per $\mu$g of DNA injected. Table III gives the results obtained.

TABLE III

| Plasmid | | | Peptide | | Cationic lipid | | Result, RLU/tumour | | |
| --- | --- | --- | --- | --- | --- | --- | --- | --- | --- |
| Reference | $\mu$g/tumour | [DNA] $\mu$g/$\mu$l | reference | pept/DNA w/w | reference | nmol/$\mu$g DNA | mean | standard deviation | n |
| pXL2622 | 10 | 0.5 | (KTPKKAKKP)$_2$ (SEQ ID NO.1) | 1.5 | (9) | 3 | 679 258 | 414 286 | 9 |
| pXL2622 | 10 | 0.5 | (KTPKKAKKP)$_2$ | " | (6) | " | 395 433 | 219 333 | 10 |
| pXL2622 | 10 | 0.5 | " | " | (16) | " | 67 994 | 82 527 | 8 |
| pXL2622 | 10 | 0.5 | " | " | (19) | " | 59 209 | 54 375 | 9 |

What is claimed is:

1. A lipopolyamine in D, L or L,D form or a salt thereof, of the general formula I

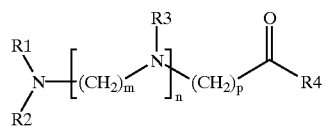

I in which:

R1, R2 and R3 represent, independently of each other, a hydrogen atom or a group —(CH$_2$)q—NRR' with q able to range between 1, 2, 3, 4, 5 and 6, and doing so independently between the various groups R1, R2 and R3 and R and R' representing, independently of each other, a hydrogen atom or a group —(CH$_2$)q'-NH2, q' being able to range between 1, 2, 3, 4, 5 and 6, and doing so independently between the various groups R and R', m and p represent, independently of each other, an integer which may vary between 1 and 6, and n represents an integer which may vary between 0 and 6, wherein, when n is equal to 0, then at least one of R1 and R2 is other than hydrogen, and when n is greater than 1, m is able to take different values and R3 is able to take different meanings within the general formula I, and R4 represents a group of general formula II

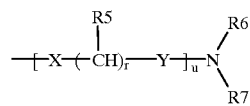

II in which:

R6 and R7 represent, independently of each other, a hydrogen atom or a saturated or unsaturated C10 to C22 aliphatic radical with at least one of the two groups being other than hydrogen, u is an integer chosen between 0 and 10 with, when u is an integer greater than 1, R5, X, Y and r able to have different meanings within the different units (X-(CHR5)r-Y)

X represents an oxygen or sulphur atom or an amine group,

Y represents a carbonyl group or a methylene group

R5 represents a hydrogen atom or a side chain of a natural amino acid, which is substituted if necessary, and r represents an integer ranging between 1 and 10 with, when r is equal to 1, R5 representing a side chain of a substituted or unsubstituted natural amino acid and, when r is greater than 1, R5 representing a hydrogen atom.

2. The lipopolyamine according to claim 1, selected from the group consisting of the following formulae

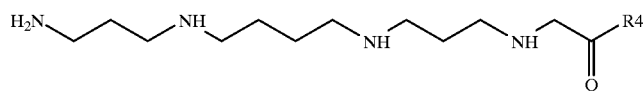

III

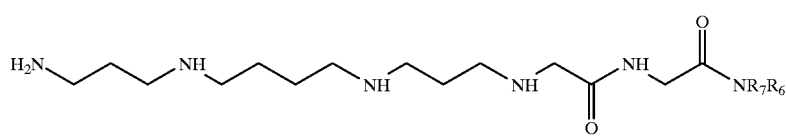

IV

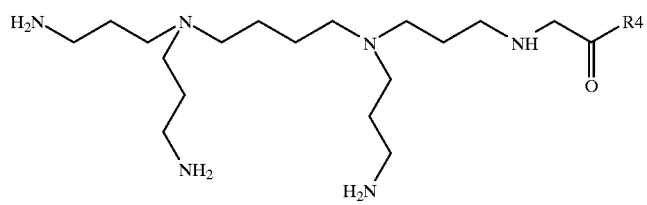

V

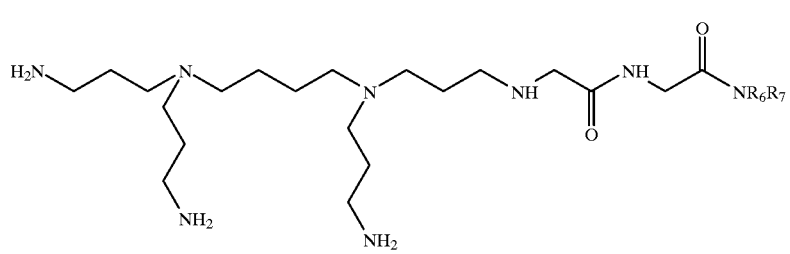

VI

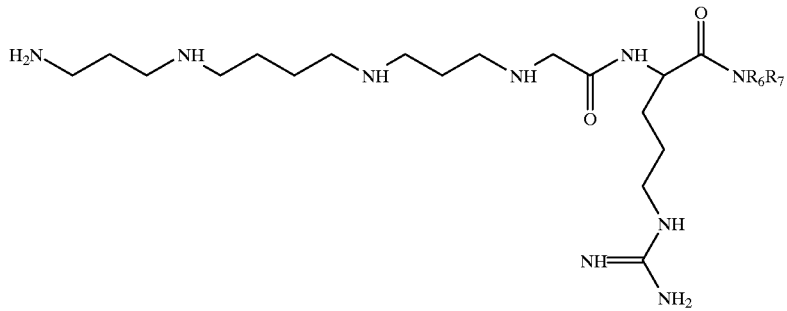

VII

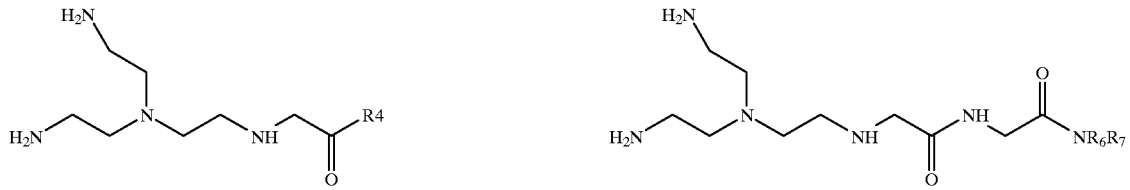

VIII          IX

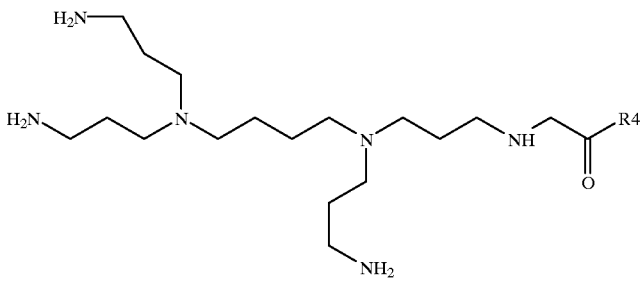

X and

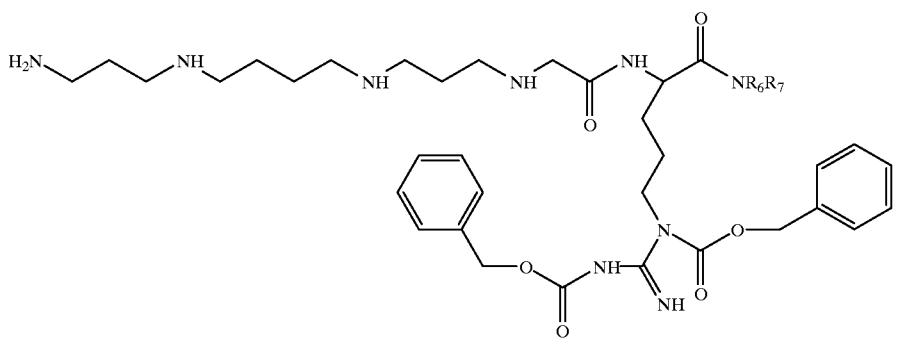

XI in which R4, R6 and R7 are defined as in claim 1.

3. A lipopolyamine according to claim 2, characterized in that R4 represents therein an NR6R7 group with R6 and R7 appearing in subformulae III to XII as an identical group selected from the group consisting of $(CH_2)_{17}CH_3$, $(CH_2)_{11}CH_3$, $(CH_2)_{13}CH_3$ and $(CH_2)_{12}CH_3$.

4. A lipopolyamine according to claim 1, characterized in that it is combined with an extra- or intracellular targeting element.

5. A lipopolyamine according to claim 4, characterized in that it incorporates the targeting element in the amino acid side chain featured by substituent R5.

6. A lipopolyamine according to claim 4, characterized in that it is a ligand of a cell receptor present at a surface of a target cell.

7. A lipopolyamine according to claim 4, characterized in that the targeting element is represented by a nuclear localization signal sequence.

8. A lipopolyamine according to claim 1, characterized in that it it is selected from the group consisting of:

$H_2N(CH_2)_3NH(CH_2)_4NH(CH_2)_3NHCH_2COGlyN[(CH_2)_{17}-CH_3]_2$ $H_2N(CH_2)_3NH(CH_2)_4NH(CH_2)_3NHCH_2CON[(CH_2)_{17}-CH_3]_2$ $H_2N(CH_2)_3NH(CH_2)_4NH(CH_2)_3NHCH_2COArgN[(CH_2)_{17}-CH_3]_2$ $H_2N(CH_2)_3NH(CH_2)_4NH(CH_2)_3NHCH_2COArg(Z)_2N[(CH_2)_{17}-CH_3]_2$ $H_2N(CH_2)_3NH(CH_2)_4NH(CH_2)_3NHCH_2COLys(rhodamine)N[(CH_2)_{17}-CH_3]_2$ $H_2N(CH_2)_3NH(CH_2)_4NH(CH_2)_3NHCH_2COLys(biotinyl)N[(CH_2)_{17}-CH_3]_2$ $\{H_2N(CH_2)_3\}_2N(CH_2)_4N\{(CH_2)_3NH_2\}(CH_2)_3NHCH_2COGlyN[(CH_2)_{17}-CH_3]_2$ {H$_2$N(CH$_2$)$_3$}$_2$N(CH$_2$)$_4$N{(CH$_2$)$_3$NH$_2$}(CH$_2$)$_3$NHCH$_2$CON[(CH$_2$)$_{17}$—CH$_3$]$_2$ {H$_2$N(CH$_2$)$_2$}$_2$N(CH$_2$)$_2$NHCH$_2$COGlyN[(CH$_2$)$_{17}$—CH$_3$]$_2$

{H$_2$N(CH$_2$)$_2$}$_2$N(CH$_2$)$_2$NHCH$_2$CON[(CH$_2$)$_{17}$—CH$_3$]$_2$

H$_2$N(CH$_2$)$_3$NH(CH$_2$)$_4$NH(CH$_2$)$_3$NHCH$_2$COGlyN[(CH$_2$)$_{17}$]$_2$

H$_2$N(CH$_2$)$_3$NH(CH$_2$)$_4$NH(CH$_2$)$_3$NHCH$_2$CON[(CH$_2$)$_{17}$]$_2$

H$_2$N(CH$_2$)$_3$NH(CH$_2$)$_4$NH(CH$_2$)$_3$NHCH$_2$COArgN[(CH$_2$)$_{17}$]$_2$

H$_2$N(CH$_2$)$_3$NH(CH$_2$)$_4$NH(CH$_2$)$_3$NHCH$_2$COArg(Z)$_2$N[(CH$_2$)$_{17}$—CH$_3$]$_2$

H$_2$N(CH$_2$)$_3$NH(CH$_2$)$_4$NH(CH$_2$)$_3$NHCH$_2$COLys(rhodamine)N[(CH$_2$)$_{17}$—CH$_3$]$_2$ H$_2$N(CH$_2$)$_3$NH(CH$_2$)$_4$NH(CH$_2$)$_3$NHCH$_2$COLys(biotinyl)N[(CH$_2$)$_{17}$—CH$_3$]$_2$ {H$_2$N(CH$_2$)$_3$}$_2$N(CH$_2$)$_4$N{(CH$_2$)$_3$NH$_2$}(CH$_2$)$_3$NHCH$_2$COGlyN[(CH$_2$)$_{17}$—CH$_3$]$_2$ {H$_2$N(CH$_2$)$_3$}$_2$N(CH$_2$)$_4$N{(CH$_2$)$_3$NH$_2$}(CH$_2$)$_3$NHCH$_2$CON[(CH$_2$)$_{17}$—CH$_3$]$_2$ {H$_2$N(CH$_2$)$_2$}$_2$N(CH$_2$)$_2$NHCH$_2$COGlyN[(CH$_2$)$_{17}$—CH$_3$]$_2$

{H$_2$N(CH$_2$)$_2$}$_2$N(CH$_2$)$_2$NHCH$_2$CON[(CH$_2$)$_{17}$—CH$_3$]$_2$

NH$_2$(CH$_2$)$_3$NH(CH$_2$)$_4$N[(CH$_2$)$_3$NH$_2$]CH$_2$COGlyN[(CH$_2$)$_{17}$CH$_3$]$_2$

NH$_2$(CH$_2$)$_3$NH(CH$_2$)$_4$NH(CH$_2$)$_3$NHCH$_2$COLysN[(CH$_2$)$_{17}$CH$_3$]$_2$

NH$_2$(CH$_2$)$_3$NH(CH$_2$)$_4$NH(CH$_2$)$_3$NHCH$_2$COLys [Cl—Z]N[(CH$_2$)$_{17}$CH$_3$]$_2$

NH$_2$(CH$_2$)$_3$NH(CH$_2$)$_4$NH(CH$_2$)$_3$NHCH$_2$COLys [CHO]N[(CH$_2$)$_{17}$CH$_3$]$_2$

NH$_2$(CH$_2$)$_3$NH(CH$_2$)$_4$NH(CH$_2$)$_3$NHCH$_2$COLys [Cholesteryl]N[(CH$_2$)$_{17}$CH$_3$]$_2$ NH$_2$(CH$_2$)$_3$NH(CH$_2$)$_4$NH(CH$_2$)$_3$NHCH$_2$COLys [Arachidonyl]N[(CH$_2$)$_{17}$CH$_3$]$_2$ NH$_2$(CH$_2$)$_3$NH(CH$_2$)$_4$NH(CH$_2$)$_3$NHCH$_2$COGluN[(CH$_2$)$_{17}$CH$_3$]$_2$ NH$_2$(CH$_2$)$_3$NH(C$_2$)$_4$NH(CH$_2$)$_3$NHCH$_2$COGlu [N(CH$_3$)$_2$]N[(CH$_2$)$_{17}$CH$_3$]$_2$ NH$_2$(CH$_2$)$_3$NH(CH$_2$)$_4$NH(CH$_2$)$_3$NHCH$_2$COGlu [O—Bz]N[(CH$_2$)$_{17}$CH$_3$]$_2$ NH$_2$(CH$_2$)$_3$NH(CH$_2$)$_4$NH(CH$_2$)$_3$NHCH$_2$COGlu [Galactosamide]N[(CH$_2$)$_{17}$CH$_3$]$_2$ NH$_2$(CH$_2$)$_3$NH(CH$_2$)$_4$NH(CH$_2$)$_3$NHCH$_2$COGlu [Glucosamide]N[(CH$_2$)$_{17}$CH$_3$]$_2$ NH$_2$(CH$_2$)$_3$NH(CH$_2$)$_4$NH(CH$_2$)$_3$NHCH$_2$COGlu [Mannosamide]N[(CH$_2$)$_{17}$CH$_3$]$_2$ NH$_2$(CH$_2$)$_3$NH(CH$_2$)$_4$NH(CH$_2$)$_3$NH(CH$_2$)$_3$CON[(CH$_2$)$_{17}$CH$_3$]$_2$ NH$_2$(CH$_2$)$_3$NH(CH$_2$)$_4$NH(CH$_2$)$_3$NHCH$_2$CONH(CH$_2$)$_5$CON[(CH$_2$)$_{17}$CH$_3$]$_2$ NH$_2$(CH$_2$)$_3$NH(CH$_2$)$_4$NH(CH$_2$)$_3$NHCH$_2$COGlyN[(CH$_2$)$_{11}$CH$_3$]$_2$ NH$_2$(CH$_2$)$_3$NH(CH$_2$)$_4$NH(CH$_2$)$_3$NHCH$_2$COGlyN[(CH$_2$)$_{11}$CH$_3$]$_2$ NH$_2$(CH$_2$)$_3$NH(CH$_2$)$_4$NH(CH$_2$)$_3$NHCH$_2$COGlyN[(CH$_2$)$_{12}$CH$_3$]$_2$ and NH$_2$(CH$_2$)$_3$NH(CH$_2$)$_4$NH(CH$_2$)$_3$NHCH$_2$COGlyN[(CH$_2$)$_{13}$CH$_3$]$_2$.

9. A pharmaceutical composition, comprising at least one lipopolyamine according to claim 1 and at least one nucleic acid.

10. The composition according to claim 9, characterized in that the nucleic acid is a deoxyribonucleic acid.

11. The composition according to claim 9, characterized in that the nucleic acid is a ribonucleic acid.

12. The composition according to claim 9, characterized in that the nucleic acid is chemically modified.

13. The composition according to claim 9, characterized in that the nucleic acid is an antisense sequence.

14. The composition according to claim 9, characterized in that the nucleic acid contains a therapeutic gene.

15. A pharmaceutical composition comprising a nucleic acid, a lipopolyamine according to claim 1 and an adjuvant, wherein the lipopolyamine and nucleic acid associate to form a lipopolyamine/nucleic acid complex and the adjuvant combines with the lipopolyamine/nucleic acid complex.

16. A composition according to claim 15, characterized in that the adjuvant is one or more neutral lipids.

17. A composition according to claim 16, characterized in that the neutral lipid or lipids are selected from the group consisting of natural zwitterionic lipids, synthetic zwitterionic lipids, and lipids lacking any ionic charge under physiological conditions.

18. A composition according to claim 17, characterized in that the neutral lipid or lipids are lipids with 2 fatty chains.

19. A composition according to claim 15, characterized in that it comprises from 0.01 to 20 equivalents of adjuvant per one equivalent of nucleic acid on a weight/weight basis.

20. A composition according to claim 9, characterized in that it comprises a vehicle which is pharmaceutically acceptable for an injectable formulation.

21. A composition according to claim 9, characterized in that it comprises a vehicle which is pharmaceutically acceptable for an application to the skin and/or the mucous membranes.

22. A process for the preparation of a lipopolyamine according to claim 1, comprising the step of coupling at least one lipid moiety with at least one asymmetric polyamine moiety, wherein the asymmetric polyamine moiety was obtained by bimolecular reaction between an alkylating agent covalently attached to a solid support and a symmetric polyamine.

23. The process according to claim 22, characterized in that the coupling of the lipid moiety with the asymmetric polyamine moiety is carried out on the solid support to which the asymmetric polyamine moiety is bound and in that the lipopolyamine thus obtained is recovered.

24. The process according to claim 23, characterized in that it involves the introduction of labelling agents, sugars or fluorescent probes onto the lipopolyamine.

25. A method for the transfection of cells comprising contacting a cell with the composition of claim 9.

26. The lipopolyamine according to claim 4, wherein the targeting element is selected from the group consisting of sugars, peptides, oligonucleotides, steroids, and lipids.

27. The lipopolyamine of claim 26 wherein the targeting element is selected from the group consisting of antibodies, antibody fragments, cell receptor ligands, fragments of cell receptor ligands, receptors, and receptor fragments.

28. The lipopolyamine of claim 27 wherein the targeting element is selected from the group consisting of ligands for growth factor receptors, ligands for cytokine receptors, ligands for cell lectin receptors, ligands for receptors for adhesion proteins, integrin receptors, transferrin receptors, HDL lipid receptors, and LDL lipid receptors.

29. The lipopolyamine of claim 1 further comprising a labelling agent selected from the group consisting of biotin, rhodamine, folate, folate derivatives, linear peptides, cyclic peptides, and pseudopeptide sequences containing the Arg-Gly-Asp epitope.

30. A pharmaceutical composition for the transfection of nucleic acid comprising a nucleic acid, a lipopolyamine according to claim 1 and an adjuvant, wherein the presence of the adjuvant increases the transfection power over the transfection power in the absence of adjuvant.

31. The composition of claim 17, wherein the neutral lipid or lipids are selected from the group consisting of dioleoylphosphatidylethanolamine (DOPE); oleoylpalmitoylphosphatidylethanolamine (POPE); distearoyl, -palmitoyl, -myristoyl phosphatidyl-ethanolamine; phosphatidylglycerols; diacylglycerols; glycosyldiacylglycerols; cerebrosides; sphingolipids; and asialogangliosides.

32. The composition of claim 30, wherein the adjuvant is a compound involved in the condensation of the nucleic acid.

33. A composition according to claim 32, characterized in that the said compound is derived partly or totally from a histone, from a nucleoline and/or from a protamine.

34. A composition according to claim 32, characterized in that the compound comprises peptide units (KTPKKAKKP) and/or (ATPAKKAA) repeated continuously or non-continuously, and wherein the number of peptide units ranges between 2 and 10.

* * * * *